(12) United States Patent
Dou et al.

(10) Patent No.: US 11,877,873 B2
(45) Date of Patent: Jan. 23, 2024

(54) SYSTEMS AND METHODS FOR DETERMINING SCANNING PARAMETER IN IMAGING

(71) Applicant: SHANGHAI UNITED IMAGING HEALTHCARE CO., LTD., Shanghai (CN)

(72) Inventors: Shidan Dou, Shanghai (CN); Xiaolin Meng, Shanghai (CN); Chuanfeng Lyu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 436 days.

(21) Appl. No.: 16/904,596

(22) Filed: Jun. 18, 2020

(65) Prior Publication Data

US 2020/0320326 A1 Oct. 8, 2020

Related U.S. Application Data

(63) Continuation of application No. PCT/CN2018/121811, filed on Dec. 18, 2018.

(30) Foreign Application Priority Data

Dec. 18, 2017 (CN) .......................... 201711365656.3
Dec. 18, 2017 (CN) .......................... 201711368029.5

(51) Int. Cl.
*G06K 9/00* (2022.01)
*A61B 6/03* (2006.01)
(Continued)

(52) U.S. Cl.
CPC ............... *A61B 6/032* (2013.01); *G06N 3/08* (2013.01); *G06T 7/0012* (2013.01); *G06T 7/11* (2017.01); *G06T 2207/20081* (2013.01)

(58) Field of Classification Search
None
See application file for complete search history.

(56) References Cited

U.S. PATENT DOCUMENTS 6,195,409 B1 2/2001 Chang et al.
2003/0179427 A1 9/2003 Lewis et al.
(Continued)

FOREIGN PATENT DOCUMENTS

CN 101305920 A 11/2008
CN 102760228 A 10/2012
(Continued)

OTHER PUBLICATIONS

The Extended European Search Report in European Application No. 18892748.7 dated Nov. 19, 2020, 8 pages.
(Continued)

*Primary Examiner* — Wei Wen Yang
(74) *Attorney, Agent, or Firm* — METIS IP LLC

(57) ABSTRACT

Systems and methods for determining at least one scanning parameter for a scanning by an imaging device (110) are provided. The methods may include obtaining a scout image of at least one portion of a subject (502), and determining, in the scout image, a region of interest (ROI) corresponding to the at least one portion of the subject (504). The methods may further include determining, based on the ROI, the at least one scanning parameter associated with the at least one portion of the subject for performing the scanning by the imaging device (506). Systems and methods for evaluating a scanning parameter are further provided. The methods may include determining a scanning parameter associated with the ROI (1606) and obtaining a reference scanning parameter associated with the ROI (1608). The methods may further include determining whether the scanning parameter
(Continued)

needs to be adjusted by comparing the scanning parameter and the reference scanning parameter (1610).

20 Claims, 17 Drawing Sheets

(51) Int. Cl.
*G06T 7/11* (2017.01)
*G06N 3/08* (2023.01)
*G06T 7/00* (2017.01)

(56) References Cited

U.S. PATENT DOCUMENTS

| | | | |
|---|---|---|---|
| 2007/0053480 | A1 | 3/2007 | Nishide et al. |
| 2008/0159611 | A1 | 7/2008 | Tao et al. |
| 2009/0128553 | A1* | 5/2009 | Perry ............... A61B 5/055 |
| | | | 345/419 |
| 2013/0105699 | A1 | 5/2013 | Asma et al. |
| 2013/0336553 | A1* | 12/2013 | Buisseret ............ G06T 7/60 |
| | | | 382/128 |
| 2015/0139520 | A1 | 5/2015 | Senegas et al. |
| 2015/0320399 | A1 | 11/2015 | Chono et al. |
| 2016/0038113 | A1* | 2/2016 | Fan ................. A61B 6/542 |
| | | | 378/19 |
| 2016/0125607 | A1 | 5/2016 | Gulaka et al. |
| 2017/0135652 | A1 | 5/2017 | Dirisio |
| 2019/0209871 | A1* | 7/2019 | O'Brien ............. A61B 6/04 |

FOREIGN PATENT DOCUMENTS

| | | |
|---|---|---|
| CN | 103150556 A | 6/2013 |
| CN | 104173071 A | 12/2014 |
| CN | 104200521 A | 12/2014 |
| CN | 104424629 A | 3/2015 |
| CN | 105433971 A | 3/2016 |
| CN | 105496563 A | 4/2016 |
| CN | 106203237 A | 12/2016 |
| CN | 106960199 A | 7/2017 |
| CN | 107273885 A | 10/2017 |
| CN | 107316307 A | 11/2017 |
| CN | 107833248 A | 3/2018 |
| CN | 108109170 A | 6/2018 |
| EP | 1216661 A2 | 6/2002 |

OTHER PUBLICATIONS

International Search Report in PCT/CN2018/121811 dated Mar. 25, 2019, 5 pages.
Written Opinion in PCT/CN2018/121811 dated Mar. 25, 2019, 5 pages.
Wang Mingpeng, CT Examination Technology, Fudan University Press, 2004, 7 pages.
Liu, Yuliang et al., Deep Matching Prior Network: Toward Tighter Multi-oriented Text Detection, 2017 IEEE Conference on Computer Vision and Pattern Recognition, 3454-3461, 2017.
Huang, Zhiwei, Research on 3D Modeling Technology Based on CT Scanning Data, China Excellent Master's Thesis Full-text Database (Electronic Journal) Information Technology Series, 2015, 71 pages.
Thorsten Heusser et al., CT Data Completion Based on Prior Scans, 2012 IEEE Nuclear Science Symposium and Medical Imaging Conference Record, 2969-2976, 2012.
First Office Action in Chinese Application No. 201711368029.5 dated Apr. 6, 2021, 15 pages.
First Office Action in Chinese Application No. 201711365656.3 dated Jan. 6, 2021, 12 pages.

* cited by examiner

SYSTEMS AND METHODS FOR DETERMINING SCANNING PARAMETER IN IMAGING

CROSS-REFERENCE TO RELATED APPLICATIONS

The present application is a continuation of International Application No. PCT/CN2018/121811, filed on Dec. 18, 2018, which designates the United States of America and claims priority of Chinese Application No. 201711368029.5, filed on Dec. 18, 2017, and Chinese Application No. 201711365656.3, field on Dec. 18, 2017, the contents of each of which are hereby incorporated by reference.

TECHNICAL FIELD

The present disclosure generally relates to imaging technology, and more particularly, relates to systems and methods for automated determination of at least one scanning parameter for a scanning by an imaging device.

BACKGROUND

Medical imaging technology has been widely used for clinical examination and medical diagnosis in recent decades. In a medical scanning, a subject may lie on a scanning table. An operator may manually determine at least one scanning parameter for the medical scanning, such as a scanning direction and/or a scanning scope. A medical imaging device may perform the medical scanning according to the scanning scope. Manual operations involved in the determination of the scanning scope may decrease the efficiency and accuracy of the medical scan. Thus, it is desirable to provide systems and methods for automatically determining one or more scanning parameter, such as the scanning scope, for a scanning by an imaging device.

SUMMARY

According to an aspect of the present disclosure, a method for determining at least one scanning parameter for a scanning by an imaging device is provided. The method may be implemented on a machine having at least one processor and a storage device. The method may include obtaining a scout image of at least one portion of a subject and determining, in the scout image, a region of interest (ROI) corresponding to the at least one portion of the subject. The method may further include determining, based on the ROI, the at least one scanning parameter associated with the at least one portion of the subject for performing the scanning by the imaging device.

In some embodiments, determining an ROI from the scout image may include segmenting the scout image using a target segmentation model.

In some embodiments, the target segmentation model may be a trained neural network model.

In some embodiments, the target segmentation model may be trained according to a training process. The training process may include obtaining a plurality of training samples, each of the plurality of training samples including a sample scout image and a label associated with one or more sample regions segmented from the sample scout image. The training process may further include using the plurality of training samples to obtain the target segmentation model.

In some embodiments, the at least one scanning parameter may include a scanning scope. The determining, based on the ROI, the at least one scanning parameter, may include determining, based on a contour of the ROI, a frame encompassing the ROI, and determining, based on the frame, the scanning scope associated with the ROI.

In some embodiments, the determining, based on a contour of the ROI, a frame encompassing the ROI, may include generating, based on a plurality of points on the contour of the ROI, the frame encompassing the ROI.

In some embodiments, the determining, based on the frame, the scanning scope associated with the ROI may include obtaining an adjusted frame by adjusting at least a portion of the frame, and designating the adjusted frame as the scanning scope associated with the ROI.

In some embodiments, the at least one scanning parameter may include a scanning direction and a scanning scope. The determining, based on the ROI, the at least one scanning parameter, may include determining a reference ROI adjacent to the ROI in the scout image using the target segmentation model, determining the scanning direction based on the reference ROI, and determining, based on the scanning direction and a contour of the ROI, the scanning scope associated with the ROI.

In some embodiments, the determining the scanning direction based on the reference ROI may include determining a plurality of reference feature points on a contour of the reference ROI, and determining, based on the plurality of reference feature points on the contour of the reference ROI, the scanning direction.

In some embodiments, the determining, based on the scanning direction and a contour of the ROI, the scanning scope associated with the ROI may include determining, based on the scanning direction, a plurality of feature points on the contour of the ROI. The determining, based on the scanning direction and a contour of the ROI, the scanning scope associated with the ROI may further include determining a plurality of lines along the scanning direction. Each of the plurality of lines may pass through one of the plurality of feature points on the contour of the ROI. The determining, based on the scanning direction and a contour of the ROI, the scanning scope associated with the ROI may further include determining, based on the plurality of lines, a frame encompassing the ROI as the scanning scope associated with the ROI.

In some embodiments, the at least one scanning parameter may include a scanning direction associated with the ROI and a scanning scope associated with the ROI. The determining, based on the ROI, the at least one scanning parameter, may include determining, based on the ROI, the scanning direction associated with the ROI. The determining, based on the ROI, the at least one scanning parameter, may further include determining, based on the scanning direction and the contour of the ROI, the scanning scope associated with the ROI.

In some embodiments, determining a scanning direction based on the ROI may include determining, based on the ROI, one or more feature vectors associated with one or more features in the ROI, and determining, based on the one or more feature vectors, the scanning direction.

In some embodiments, the determining one or more feature vectors based on the ROI may include determining, based on the ROI, a covariance matrix indicating a difference between pixels in the ROI in the one or more features, and determining, based on the covariance matrix, the one or more feature vectors.

In some embodiments, the method may further include obtaining a reference scanning parameter for each of the at least one scanning parameter associated with the ROI, and determining whether a scanning parameter of the at least one scanning parameter needs to be adjusted by comparing the scanning parameter with the corresponding reference scanning parameter.

According to another aspect of the present disclosure, a system for determining at least one scanning parameter for a scanning by an imaging device is provided. The system may include at least one non-transitory storage medium including a set of instructions, and at least one processor in communication with the at least one non-transitory storage medium. When executing the set of instructions, the at least one processor may be configured to cause the system to obtain a scout image of at least one portion of a subject, and determine, in the scout image, a region of interest (ROI) corresponding to the at least one portion of the subject. The at least one processor may be further configured to cause the system to determine, based on the ROI, the at least one scanning parameter associated with the at least one portion of the subject for performing the scanning by the imaging device.

According to yet another aspect of the present disclosure, a system for determining at least one scanning parameter for a scanning by an imaging device is provided. The system may include an obtaining module, configured to obtain a scout image of at least one portion of a subject. The system may further include a segmentation module, configured to determine, in the scout image, a region of interest (ROI) corresponding to the at least one portion of the subject. The system may further include a determination module, configured to determine, based on the ROI, the at least one scanning parameter associated with the at least one portion of the subject for performing the scanning by the imaging device.

According to still another aspect of the present disclosure, a non-transitory computer readable medium is provided. The non-transitory computer readable medium comprising at least one set of instructions for determining at least one scanning parameter for a scanning by an imaging device. When executed by at least one processor of a computing device, the at least one set of instructions may direct the at least one processor to obtain a scout image of at least one portion of a subject and determine, in the scout image, a region of interest (ROI) corresponding to the at least one portion of the subject. The at least one set of instructions may further direct the at least one processor to determine, based on the ROI, the at least one scanning parameter associated with the at least one portion of the subject for performing the scanning by the imaging device.

According to another aspect of the present disclosure, a method for determining one or more scanning scopes for a scanning by an imaging device is provided. The method may be implemented on a machine having at least one processor and a storage device. The method may include obtaining a scout image of at least one portion of a subject, and determining, in the scout image, a region of interest (ROI) corresponding to the at least one portion of the subject. The method may further include determining one or more reference regions associated with the ROI from the scout image, and determining, based on a first contour of the ROI and a second contour of each of the one or more reference regions, the scanning scope associated with the ROI for performing the scanning by the imaging device.

In some embodiments, the determining, based on a first contour of the ROI region and a second contour of each of the one or more reference regions, the scanning scope associated with the ROI may include determining, based on the second contour of each of the one or more reference regions, a scanning direction associated with the ROI. The determining, based on a first contour of the ROI region and a second contour of each of the one or more reference regions, the scanning scope associated with the ROI, may further include determining, based on the scanning direction and the first contour of the ROI, the scanning scope.

In some embodiments, the one or more reference regions may include a first reference region. The determining, based on the second contour of each of the one or more reference regions, a scanning direction associated with the ROI, may include determining a plurality of reference feature points on the second contour of the first reference region, and determining, based on the plurality of reference feature points on the second contour of the first reference region, the scanning direction.

In some embodiments, the one or more reference regions may include a first reference region and a second reference region. The determining, based on the second contour of each of the one or more reference regions, a scanning direction associated with the ROI, may include determining a first point on the second contour of the second reference region, and determine, based on the first point on the second contour of the second reference region, a second point on the second contour of the first reference region. The second point may be an intersection point of the second contour of the first reference region and a feature line passing through the first point, and determine, based on the second point and a third point on the second contour of the first reference region, the scanning direction.

In some embodiments, the determining, based on the scanning direction and the first contour of the ROI, the scanning scope associated with the ROI, may include determining, based on the first contour of the ROI and the scanning direction, a frame encompassing the ROI. The scanning scope associated with the ROI, may further include determining the scanning scope based on the frame.

In some embodiments, the determining, based on the first contour of the ROI and the scanning direction, a frame encompassing the ROI, may include determining, based on the scanning direction, a plurality of feature points on the first contour of the ROI, and determining a plurality of lines along the scanning direction. Each of the plurality of lines may passing through one of the plurality of feature points on the first contour of the ROI. The determining, based on the first contour of the ROI and the scanning direction, a frame encompassing the ROI, may further include determining, based on the plurality of lines, the frame associated with the ROI.

In some embodiments, the determining the scanning scope based on the frame may include obtaining an adjusted frame by adjusting one or more sides of the frame, and designating the adjusted frame as the scanning scope.

According to yet another aspect of the present disclosure, a system for determining at least one scanning parameter for a scanning by an imaging device is provided. The system may include at least one non-transitory storage medium including a set of instructions, and at least one processor in communication with the at least one non-transitory storage medium. When executing the set of instructions, the at least one processor may be configured to cause the system to obtain a scout image of at least one portion of a subject, and determine, in the scout image, a region of interest (ROI) corresponding to the at least one portion of the subject. The at least one processor may be further configured to cause the system to determine one or more reference regions associated with the ROI from the scout image, and determine, based on a first contour of the ROI and a second contour of each of the one or more reference regions, the scanning scope associated with the ROI for performing the scanning by the imaging device.

According to still another aspect of the present disclosure, a system for determining at least one scanning parameter for a scanning by an imaging device is provided. The system may include an obtaining module, configured to obtain a scout image of at least one portion of a subject, and a segmentation module, configured to determine, in the scout image, a region of interest (ROI) corresponding to the at least one portion of the subject. The system may further include a determination module, configured to determine one or more reference regions associated with the ROI from the scout image, and determine, based on a first contour of the ROI and a second contour of each of the one or more reference regions, the scanning scope associated with the ROI for performing the scanning by the imaging device.

According to a further aspect of the present disclosure, a non-transitory computer readable medium is provided. The non-transitory computer readable medium may include at least one set of instructions for determining at least one scanning parameter for a scanning by an imaging device, wherein when executed by at least one processor of a computing device, the at least one set of instructions may direct the at least one processor to obtain a scout image of at least one portion of a subject, and determine, in the scout image, a region of interest (ROI) corresponding to the at least one portion of the subject. The at least one set of instructions may further direct the at least one processor to determine one or more reference regions associated with the ROI from the scout image, and determine, based on a first contour of the ROI and a second contour of each of the one or more reference regions, the scanning scope associated with the ROI for performing the scanning by the imaging device.

According to another aspect of the present disclosure, a method for evaluating a scanning parameter is provided. The method may be implemented on a machine having at least one processor and a storage device. The method may include obtaining a scout image of at least one portion of a subject, and determining, in the scout image, a region of interest (ROI) corresponding to the at least one portion of the subject. The method may further include determining, based on a contour of the ROI, a scanning parameter associated with the ROI. The method may further include obtaining a reference scanning parameter associated with the ROI and determining whether the scanning parameter needs to be adjusted by comparing the scanning parameter and the reference scanning parameter.

In some embodiments, the scanning parameter may include a scanning direction, and the determining, based on a contour of the ROI, a scanning parameter associated with the ROI, may includes determining, in the scout image, a first reference region adjacent to the ROI using a target segmentation model, and determining, based on the first reference region associated with the ROI, the scanning direction associated with the ROI.

In some embodiments, the scanning parameter may include a scanning scope. The method may further include determining, based on the scanning direction, the scanning scope associated with the ROI.

In some embodiments, the reference scanning parameter associated with the ROI may include a reference scanning direction associated with the ROI. The obtaining a reference scanning parameter associated with the ROI, may include determining, in the scout image, a second reference region adjacent to the ROI or the first referent region using the segmentation model, and determining, based on the first reference region and the second reference region associated with the ROI, the reference scanning direction associated with the ROI.

In some embodiments, the reference scanning parameter may include a reference scanning scope, and the method may further include determining, based on the reference scanning direction, the reference scanning scope associated with the ROI.

In some embodiments, the determining whether the scanning parameter needs to be adjusted by comparing the scanning parameter and the reference scanning parameter may include determining, based on a difference between the scanning parameter and the reference scanning parameter, a reliability factor of the scanning parameter. The determining whether the scanning parameter needs to be adjusted by comparing the scanning parameter and the reference scanning parameter may further include determining whether the scanning parameter needs to be adjusted by comparing the reliability factor of the scanning parameter with a threshold.

In some embodiments, the method may further include causing the machine to provide an edit option for a user based on a determination that the scanning parameter needs to be adjusted.

According to yet another aspect of the present disclosure, a system for evaluating a scanning parameter is provided. The system may include at least one non-transitory storage medium including a set of instructions and at least one processor in communication with the at least one non-transitory storage medium. When executing the set of instructions, the at least one processor may be configured to cause the system to obtain a scout image of at least one portion of a subject and determine, in the scout image, a region of interest (ROI) corresponding to the at least one portion of the subject. The at least one processor may be further configured to cause the system to determine, based on a contour of the ROI, a scanning parameter associated with the ROI, and obtain a reference scanning parameter associated with the ROI. The at least one processor may be further configured to cause the system to determine whether the scanning parameter needs to be adjusted by comparing the scanning parameter and the reference scanning parameter.

According to still another aspect of the present disclosure, a system for evaluating a scanning parameter. The system may include an obtaining module, configured to obtain a scout image of at least one portion of a subject, and a segmentation module, configured to determine, in the scout image, a region of interest (ROI) corresponding to the at least one portion of the subject. The system may further include a determination module. The determination module may be configured to determine, based on a contour of the ROI, a scanning parameter associated with the ROI, and obtain a reference scanning parameter associated with the ROI. The determination module may be further configured to determine whether the scanning parameter needs to be adjusted by comparing the scanning parameter and the reference scanning parameter.

According to a further aspect of the present disclosure, a non-transitory computer readable medium is provided. The non-transitory computer readable medium may include at least one set of instructions for evaluating a scanning parameter. When executed by at least one processor of a computing device, the at least one set of instructions may direct the at least one processor to obtain a scout image of at least one portion of a subject, and determine, in the scout image, a region of interest (ROI) corresponding to the at least one portion of the subject. The at least one set of instructions may further direct the at least one processor to determine, based on a contour of the ROI, a scanning parameter associated with the ROI. The at least one set of instructions may further direct the at least one processor to obtain a reference scanning parameter associated with the ROI, and determine whether the scanning parameter needs to be adjusted by comparing the scanning parameter and the reference scanning parameter.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
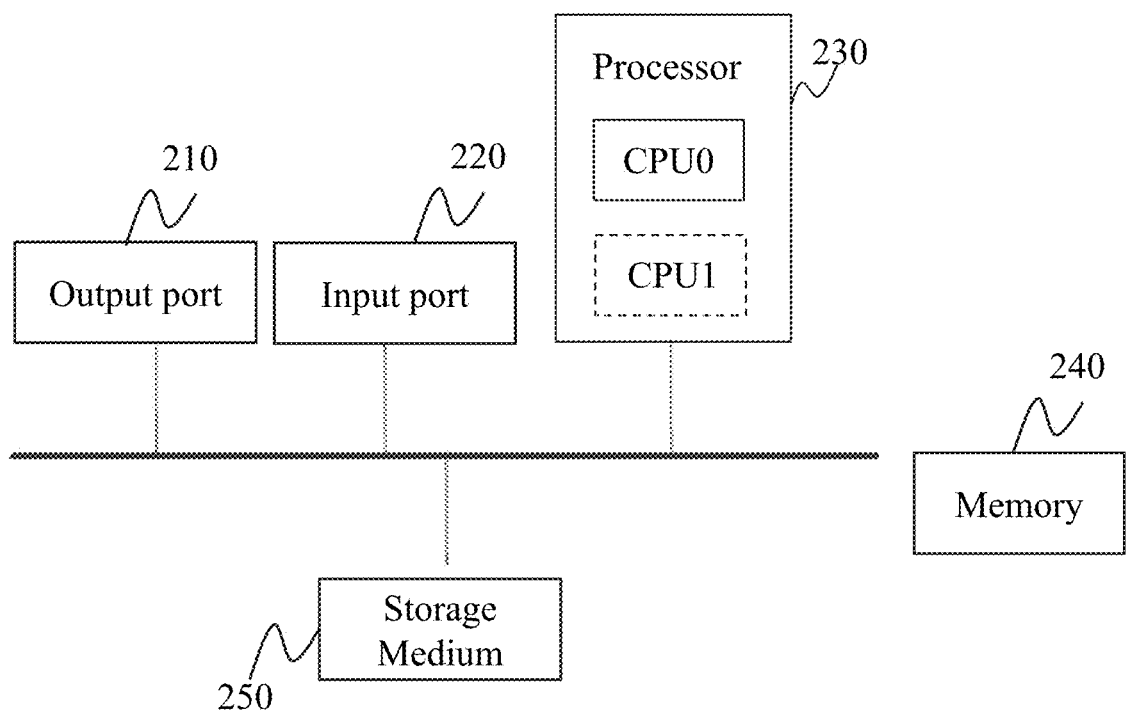
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 230 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for an imaging system. In some embodiments, the imaging system may include a single modality imaging system and/or a multi-modality imaging system. The single modality imaging system may include, for example, an X-ray imaging system, an emission computed tomography (ECT) system, a magnetic resonance imaging (MRI) system, an ultrasonography system, a positron emission tomography (PET) system, or the like, or any combination thereof. The multi-modality imaging system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a digital subtraction angiography-magnetic resonance imaging (DSA-MRI) system, etc. It should be noted that the imaging system described below is merely provided for illustration purposes, and not intended to limit the scope of the present disclosure.

The present disclosure provides mechanisms (which can include methods, systems, computer-readable medium, etc.) for automated determination of at least one scanning parameter for a scanning by an imaging device. In some embodiments, a scout image may be obtained. One or more regions in the scout image may be obtained by segmenting the scout image. The one or more regions may include a region of interest (ROI). In some embodiments, the one or more regions may further include one or more reference regions. The at least one scanning parameter may include a scanning direction and/or a scanning scope. In some embodiments, a frame for a helical scanning may be determined based on a contour of the ROI. Specifically, a frame (e.g., a minimum bounding box) encompassing the ROI may be determined based on the contour of the ROI. The frame may be adjusted (e.g., increased or reduced in size) to generate an adjusted frame. In some embodiments, for an axial scanning, a scanning direction may be determined. The scanning scope may be determined based on the contour of the ROI and a scanning direction. For example, the scanning direction may be determined based on a contour of each of the one or more reference regions. As another example, the scanning direction may be determined based on a plurality of feature vectors associated with the ROI. The feature vectors may reflect a difference between pixels (e.g., a difference in pixel coordinates) in the ROI.

The present disclosure further provides mechanisms (which can include methods, systems, computer-readable medium, etc.) for automated evaluation of a scanning parameter. A reference scanning parameter associated with the ROI may be determined for the scanning parameter associated with the ROI. The scanning parameter and the reference scanning parameter may be compared to determine whether the scanning parameter needs to be adjusted. For instance, a reliability may be determined based on a difference between the scanning parameter and the reference scanning parameter. In response to a determination that the reliability is less than a threshold, the scanning parameter may be adjusted.

Figure 1:
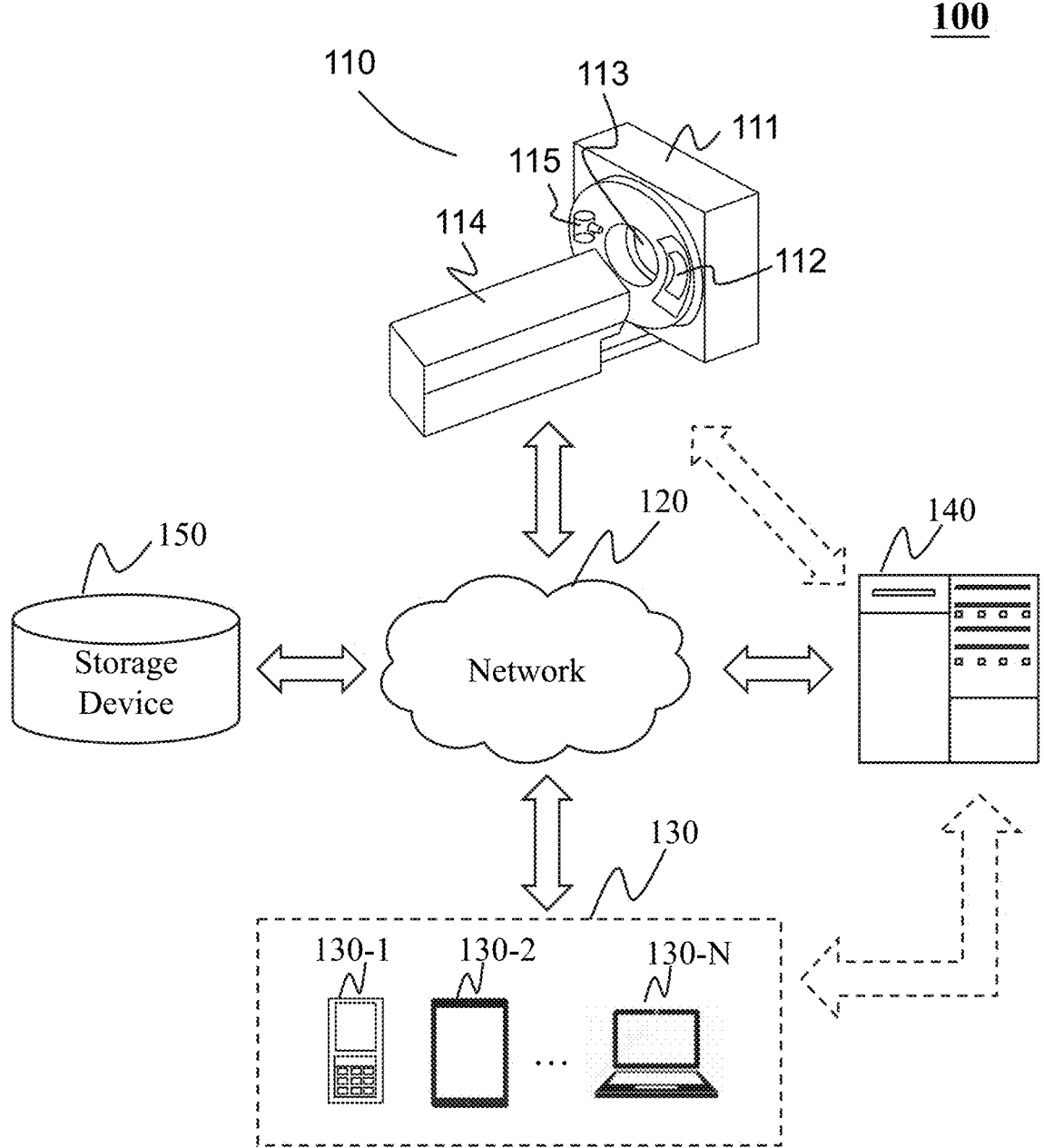
FIG. 1 is a schematic diagram illustrating an exemplary imaging system according to some embodiments of the present disclosure.

FIG. 1 is a schematic diagram illustrating an exemplary imaging system according to some embodiments of the present disclosure. The imaging system shown in FIG. 1 (i.e., the imaging system 100) may include a imaging device 110, a network 120, one or more terminals 130, a processing engine 140, and a storage device 150. In some embodiments, the imaging device 110, the terminal(s) 130, the processing engine 140, and/or the storage device 150 may be connected to and/or communicate with each other via a wireless connection (e.g., the network 120), a wired connection, or a combination thereof. The connection between the components of the imaging system 100 may be variable. Merely by way of example, the imaging device 110 may be connected to the processing engine 140 through the network 120, as illustrated in FIG. 1. As another example, the imaging device 110 may be connected to the processing engine 140 directly. As a further example, the storage device 150 may be connected to the processing engine 140 through the network 120, as illustrated in FIG. 1, or connected to the processing engine 140 directly. As still a further example, a terminal 130 may be connected to the processing engine 140 through the network 120, as illustrated in FIG. 1, or connected to the processing engine 140 directly.

The imaging device 110 may generate or provide image data via scanning a subject (e.g., a human subject) disposed on a scanning table 114 of the imaging device 110. In some embodiments, the imaging device 110 may include a single-modality scanner and/or multi-modality scanner. The single-modality scanner may include, for example, a computed tomography (CT) scanner. The multi-modality scanner may include a single photon emission computed tomography-computed tomography (SPECT-CT) scanner, a positron emission tomography-computed tomography (PET-CT) scanner, a computed tomography-ultra-sonic (CT-US) scanner, a digital subtraction angiography-computed tomography (DSA-CT) scanner, or the like, or a combination thereof. In some embodiments, the image data may include projection data, images relating to the subject, etc. The projection data may be raw data generated by the imaging device 110 by scanning the subject, or data generated by a forward projection on an image relating to the subject. In some embodiments, the subject may include a body, a substance, an object, or the like, or a combination thereof. In some embodiments, the subject may include a specific portion of a body, such as a head, a thorax, an abdomen, or the like, or a combination thereof. In some embodiments, the subject may include a specific organ or region of interest, such as an esophagus, a trachea, a bronchus, a stomach, a gallbladder, a small intestine, a colon, a bladder, a ureter, a uterus, a fallopian tube, etc.

In some embodiments, the imaging device 110 may include a gantry 111, a detector 112, a detecting region 113, a scanning table 114, and a radioactive scanning source 115. The gantry 111 may support the detector 112 and the radioactive scanning source 115. A subject may be placed on the scanning table 114 to be scanned. The radioactive scanning source 115 may emit radioactive rays to the subject. The radiation may include a particle ray, a photon ray, or the like, or a combination thereof. In some embodiments, the radiation may include a plurality of radiation particles (e.g., neutrons, protons, electron, µ-mesons, heavy ions), a plurality of radiation photons (e.g., X-ray, a γ-ray, ultraviolet, laser), or the like, or a combination thereof. The detector 112 may detect radiations and/or radiation events (e.g., gamma photons) emitted from the detecting region 113. In some embodiments, the detector 112 may include a plurality of detector units. The detector units may include a scintillation detector (e.g., a cesium iodide detector) or a gas detector. The detector unit may be a single-row detector or a multi-rows detector.

In some embodiments, the imaging device 110 may be integrated with one or more other devices that may facilitate the scanning of the subject, such as, an image-recording device. The image-recording device may be configured to take various types of images related to the subject. For example, the image-recording device may be a two-dimensional (2D) camera that takes pictures of the exterior or outline of the subject. As another example, the image-recording device may be a 3D scanner (e.g., a laser scanner, an infrared scanner, a 3D CMOS sensor) that records the spatial representation of the subject.

The network 120 may include any suitable network that can facilitate the exchange of information and/or data for the imaging system 100. In some embodiments, one or more components of the imaging system 100 (e.g., the imaging device 110, the processing engine 140, the storage device 150, the terminal(s) 130) may communicate information and/or data with one or more other components of the imaging system 100 via the network 120. For example, the processing engine 140 may obtain image data from the imaging device 110 via the network 120. As another example, the processing engine 140 may obtain user instruction(s) from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may be connected to and/or communicate with the imaging device 110, the processing engine 140, and/or the storage device 150. For example, the terminal(s) 130 may obtain a processed image from the processing engine 140. As another example, the terminal(s) 130 may obtain image data acquired via the imaging device 110 and transmit the image data to the processing engine 140 to be processed. In some embodiments, the terminal(s) 130 may include a mobile device 130-1, a tablet computer 130-2, a laptop computer 130-N, or the like, or any combination thereof. For example, the mobile device 130-1 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 130 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. The input information received through the input device may be transmitted to the processing engine 140 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 130 may be part of the processing engine 140.

The processing engine 140 may process data and/or information obtained from the imaging device 110, the storage device 150, the terminal(s) 130, or other components of the imaging system 100. For example, the processing engine 140 may reconstruct an image based on projection data generated by the imaging device 110. As another example, the processing engine 140 may determine the position of a target region (e.g., a region in a human subject) to be scanned by the imaging device 110. In some embodiments, the processing engine 140 may be a single server or a server group. The server group may be centralized or distributed. In some embodiments, the processing engine 140 may be local to or remote from the imaging system 100. For example, the processing engine 140 may access information and/or data from the imaging device 110, the storage device 150, and/or the terminal(s) 130 via the network 120. As another example, the processing engine 140 may be directly connected to the imaging device 110, the terminal(s) 130, and/or the storage device 150 to access information and/or data. In some embodiments, the processing engine 140 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing engine 140 may be implemented by a computing device 200 having one or more components as described in connection with FIG. 2.

The storage device 150 may store data, instructions, and/or any other information. In some embodiments, the storage device 150 may store data obtained from the processing engine 140, the terminal(s) 130, and/or the storage device 150. In some embodiments, the storage device 150 may store data and/or instructions that the processing engine 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the imaging system 100 (e.g., the processing engine 140, the terminal(s) 130). One or more components of the imaging system 100 may access the data or instructions stored in the storage device 150 via the network 120. In some embodiments, the storage device 150 may be part of the processing engine 140.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 150 may be a data storage including cloud computing platforms, such as public cloud, private cloud, community, and hybrid clouds, etc. However, those variations and modifications do not depart the scope of the present disclosure.

FIG. 2 is a schematic diagram illustrating exemplary hardware and/or software components of an exemplary computing device on which the processing engine 140 may be implemented according to some embodiments of the present disclosure. The computing device shown in FIG. 2 (i.e., the computing device 200) may include an output port 210, an input port 220, a processor 230, a memory 240 and a storage medium 250.

The output port 210 or the input port 220 may output or input signals, data, information, etc. In some embodiments, the output port 210 and the input port 220 may enable user interaction with the processing engine 140. In some embodiments, the output port 210 may include an output device. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof. In some embodiments, the input port 220 may include an input device. Examples of the input device may include a keyboard, a mouse, a touch screen, a microphone, or the like, or a combination thereof.

The processor 230 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 230 may process image data obtained from the imaging device 110, the terminals 130, the storage device 150, and/or any other component of the imaging system 100. In some embodiments, the processor 230 may include one or more hardware processors, such as a microcontroller, a microprocessor, a reduced instruction set computer (RISC), an application specific integrated circuits (ASICs), an application-specific instruction-set processor (ASIP), a central processing unit (CPU) as illustrated as CPU0 in FIG. 2, a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof. In some embodiments, the processor 230 may include more than one CPU, as shown by CPU1 in FIG. 2.

Merely for illustration, only one processor is described in the computing device 200. However, it should be noted that the computing device 200 in the present disclosure may also include multiple processors. Thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The memory 240 and/or the storage medium 250 may store data/information obtained from the imaging device 110, the terminals 130, the processing engine 140, and/or any other component of the imaging system 100. In some embodiments, the storage medium 250 may include a mass storage, removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the memory 240 and/or the storage medium 250 may store one or more programs and/or instructions to perform exemplary methods described in the present disclosure. For example, the storage medium 250 may store a program for the processing engine 140 for determining the position of an interested region of a subject (e.g., an interested portion of a human subject).

Figure 3:
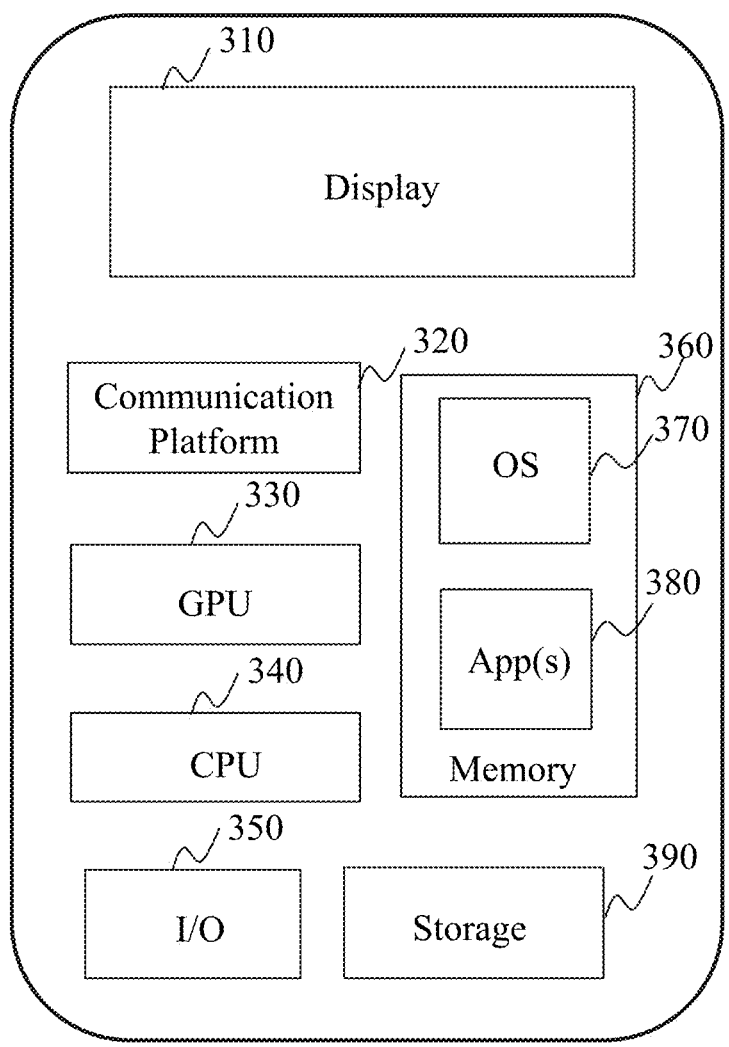
FIG. 3 is a schematic diagram illustrating hardware and/or software components of an exemplary mobile device according to some embodiments of the present disclosure.

FIG. 3 is a schematic diagram illustrating exemplary hardware and/or software components of an exemplary mobile device 300 on which the terminals 130 may be implemented according to some embodiments of the present disclosure. The mobile device shown in FIG. 3 (i.e., the mobile device 300) may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™ Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing engine 140. User interactions with the information stream may be achieved via the I/O 350 and provided to the processing engine 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
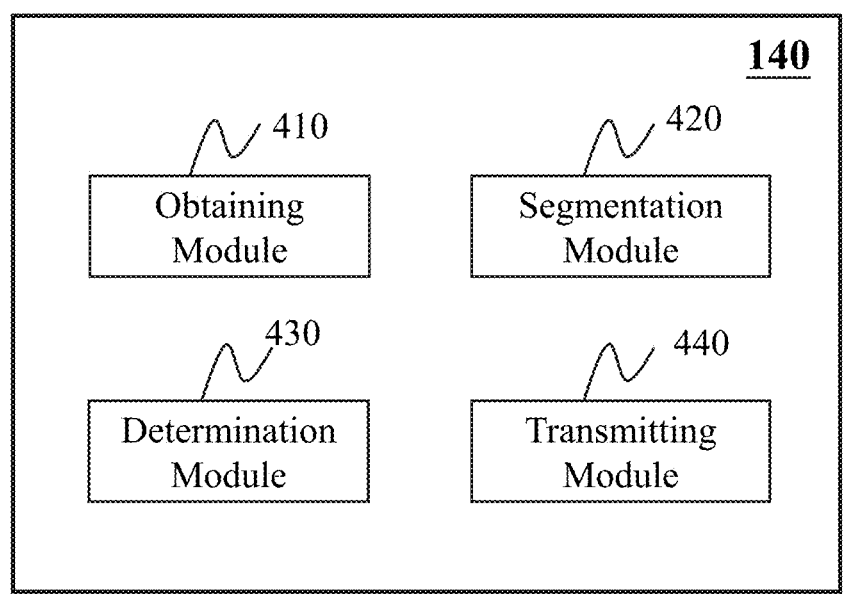
FIG. 4 is a block diagram illustrating an exemplary processing engine according to some embodiments of the present disclosure.

FIG. 4 is a block diagram illustrating an exemplary processing engine according to some embodiments of the present disclosure. In some embodiments, the processing engine 140 may include an obtaining module 410, a segmentation module 420, a determination module 430 and a transmitting module 440. The processing engine 140 may be implemented on various components of the imaging system 100 (e.g., the processor 230 of the computing device 200 illustrated in FIG. 2, the GPU 330 or CPU 340 of the mobile device 300 illustrated in FIG. 3).

The obtaining module 410 may acquire data related to the determination of a scanning scope. In some embodiments, the obtaining module 410 may acquire data from one or more components of the imaging system 100. For example, the obtaining module 410 may obtain a scout image from the storage device 150. The scout image may be used to locate a region of interest (ROI) of a subject to be scanned. The subject may include an animal, a human, a non-biological object, or the like. The ROI of an animal or a human subject may include, for example, the head, the breast, an abdomen, a leg, or the like, or a portion thereof. As another example, the obtaining module 410 may obtain a target segmentation model from the storage device 150. The target segmentation model may be used to segment the scout image.

The segmentation module 420 may segment an image. For example, the segmentation module 420 may segment the scout image using the target segmentation model, thereby determining one or more regions in the scout image. The one or more regions may be used to determine at least one scanning parameter associated with a scanning (e.g., a CT scanning, an MRI scanning, a PET scanning) by an imaging device. For instance, the at least one scanning parameter associated with the scanning may include a scanning direction, a scanning scope, or the like, or any combination thereof. In some embodiments, the segmentation module 420 may segment the scout image to obtain an ROI. For example, the ROI may be a head area of a subject, including, e.g., the skull, the brain. In some embodiments, the segmentation module 420 may obtain an ROI and a reference ROI according to the result of the segmentation of the scout image. The reference ROI may be associated with the determination of a scanning direction. Merely by way of example, the reference ROI may be adjacent to the ROI. In some embodiments, the segmentation module 420 may obtain an ROI, a first reference region (also referred to as the reference ROI), and a second reference region according to another result of the segmentation of the scout image. The first reference region and the second reference region may be associated with the determination of the scanning direction.

The determination module 430 may determine at least one scanning parameter for the scanning of the imaging device. In some embodiments, the determination module 430 may determine a frame based on a contour of the ROI. For instance, the frame may be a minimum parallelogram encompassing the ROI. The determination module 430 may further determine an adjusted frame based on the frame. For example, the adjusted frame may be determined by adjusting (e.g., extending, shrinking) one or more sides of the minimum parallelogram. In some embodiments, the determination module 430 may designate the adjusted frame as a helical scanning scope for a helical scan. In some embodiments, the determination module 430 may determine a scanning direction. In some embodiments, the determination module 430 may determine the scanning scope based on the contour of the ROI. For example, the determination module 430 may determine a frame encompassing the ROI based on a plurality of points on the contour of the ROI. The frame may be a rectangle, a parallelogram, a trapezoid, or any other shape. Merely by way of example, the frame may be a bounding box encompassing the ROI. In some embodiments, the determination module 430 may further adjust at least a portion of the frame to obtain an adjusted frame. For example, the determination module 430 may increase or reduce the size of the frame through extending or shortening at least one side of the frame by an amount. In some embodiments, the amounts of the adjustment in at least two sides of a frame (e.g., a rectangular frame) may be the same or different. The adjusted frame may be designated as the scanning scope associated with the ROI, for example, for a helical scanning by the imaging device. More descriptions regarding the determination of the scanning scope based on the contour of the ROI may be found, for example, in FIG. 8 and the descriptions thereof.

In some embodiments, the determination module 430 may determine the scanning direction associated with the ROI. The scanning scope associated with the ROI may be further determined based on a contour of the ROI and the scanning direction. Specifically, the determination module 430 may determine a plurality of feature points (e.g., two or more feature points) on the contour of the ROI. A plurality of lines along the scanning directions may be determined. Each of the plurality of lines may pass through one of the plurality of feature points. The determination module 430 may further determine a frame encompassing the ROI based on the plurality of lines. The scanning scope may be determined based on the frame. More descriptions regarding the determination of the scanning scope associated with the ROI based on the contour of the ROI and the scanning direction may be found elsewhere in the present disclosure, for example, in FIGS. 10, 13A, 13B, 14, and 15A and the descriptions thereof.

In some embodiments, the determination module 430 may determine the scanning direction based on a second contour of each of the one or more reference regions. The scanning scope associated with the ROI may be further determined based on the scanning direction and the first contour of the ROI. For example, the one or more reference regions may include a first reference region (interchangeably referred to as a "reference ROI") adjacent to the ROI. The determination module 430 may determine a plurality of reference feature points on the contour of the first reference region. The scanning direction may be determined based on the plurality of reference feature points on the contour of the first reference region. As another example, the one or more reference regions may include a first reference region and a second reference region. The determination module 430 may determine the scanning direction based on the contour of the first reference region and the contour of the second reference region. More descriptions regarding the determination of the scanning direction based on the second contour of each of the one or more reference regions may be found elsewhere in the present disclosure, for example, in FIGS. 10-12 and 18-19 and the descriptions thereof. Additionally or alternatively, the determination module 430 may determine the scanning direction based on the ROI. For instance, the determination module 430 may determine one or more feature vectors associated with one or more features in the ROI. The feature vectors may be determined based on a covariance matrix indicating a difference between pixels in the ROI in the one or more features. More descriptions regarding the determination of the scanning direction based on the ROI may be found elsewhere in the present disclosure, for example, in FIGS. 14, 15A and 15B and the descriptions thereof.

In some embodiments, the determination module 430 may determine a reference scanning parameter associated with the ROI. In some embodiments, the reference scanning parameter may be determined according to an operation that is at least partly different from the operation of determining the scanning parameter. The determination module 430 may determine whether the scanning parameter needs to be adjusted by comparing the scanning parameter and the reference scanning parameter. In some embodiments, the determination module 430 may determine a difference between the scanning parameter and the reference scanning parameter. For example, the determination module 430 may further determine a reliability factor of the scanning parameter based on the difference between the scanning parameter and the reference scanning parameter. For example, the reliability factor may have a value between 0 to 1. In some embodiments, the determination module 430 may compare the reliability factor with a threshold. In response to a determination that the reliability factor is less than the threshold, the determination module 430 may determine that the scanning parameter needs to be adjusted. An edit option may be provided to the user to modify the scanning parameter.

The transmitting module 440 may transmit information and/or an instruction to one or more components of the imaging system 100. For example, the transmitting module 440 may transmit the at least one scanning parameter determined by the determination module 430 to the imaging device 110, so that the imaging device 110 may perform a scanning according to the at least one scanning parameter. In some embodiments, in response to a determination that a scanning parameter needs to be adjusted, the transmitting module 440 may transmit a notification message to a user terminal (e.g., the user terminal 130).

It should be noted that the above description of the processing engine 140 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the processing engine 140 may include one or more additional modules. For example, the processing engine 140 may further include a storage module configured to store data generated by the above-mentioned modules in the processing engine 140. In some embodiments, one or more modules of the processing engine 140 described above may be omitted. For example, the transmitting module 440 may be omitted.

Figure 5:
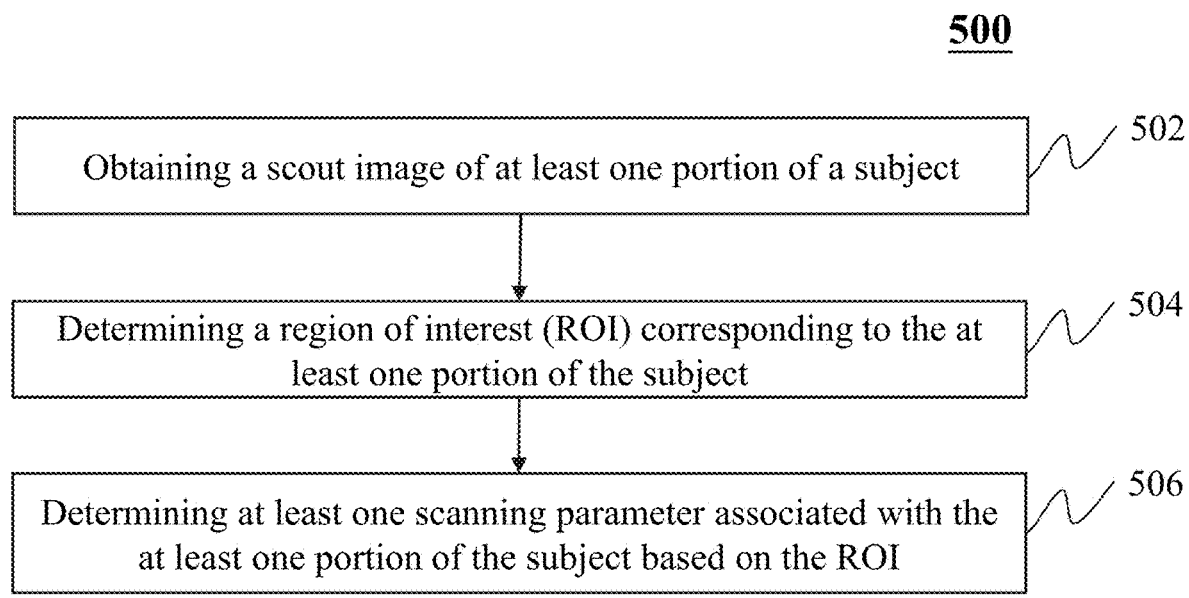
FIG. 5 is a flowchart illustrating an exemplary process for determining a scanning scope for a scanning using a target segmentation model according to some embodiments of the present disclosure.

FIG. 5 is a flowchart illustrating an exemplary process for determining a scanning scope for a scanning using a target segmentation model according to some embodiments of the present disclosure. In some embodiments, one or more operations of the process 500 illustrated in FIG. 5 may be implemented in the imaging system 100 illustrated in FIG. 1. For example, at least a part of the process 500 illustrated in FIG. 5 may be stored in the storage device 150 in the form of instructions, and invoked and/or executed by the processing engine 140 (e.g., the processor 230 of the computing device 200 as illustrated in FIG. 2, the GPU 330 or CPU 340 of the mobile device 300 as illustrated in FIG. 3).

In 502, the processing engine 140 (e.g., the obtaining module 410) may obtain a scout image of at least one portion of a subject. As used herein, a "scout image" refers to an image obtained to assist in the planning of a scanning by an imaging device (e.g., a medical imaging device). For example, the scout image may be used to locate an ROI of a subject for a scanning. The subject may include an animal, a human, or a non-biological object, etc. The ROI of an animal or a human may include, for example, the head, the chest, the abdomen, a breast, a leg, or the like, or a portion thereof, or a combination thereof, of a subject.

The scout image may be obtained by a pre-scanning. The pre-scanning may be a CT scanning, an MR scanning, a PET scanning, or the like, or a combination thereof. In some embodiments, the scout image may be obtained according to a position indicator. The position indicator may include a laser position indicator. For instance, the laser position indicator may emit laser rays to at least one portion of the subject to mark a starting position and an ending position. The at least one portion of the subject may include the ROI. The imaging device 110 may perform the pre-scanning from the starting position to the ending position. In some embodiments, a scanning (a subsequent scanning after the pre-scanning) may be performed on the ROI to obtain information (e.g., diagnostic information) related to the ROI. The scanning may include a CT scanning, an MRI scanning, a PET scanning, or the like, or a combination thereof. For instance, when a surgery needs to be performed or has been performed on the head of the subject (e.g., a patient) to remove a tumor in the head, a pre-scanning may be performed on the subject to obtain a scout image of the head (i.e., the ROI). Then a subsequent scanning may be performed on the head based on the scout image. Information related to the surgery may be determined based on scan data associated with the subsequent scanning, such as the position and/or the volume of the tumor to be removed, a result of the surgery (e.g., whether the entire tumor has been removed), the recovery status of the subject after the surgery (e.g., whether a new tumor has grown in the head), or the like, or any combination thereof.

Figure 6:
FIG. 6 is an exemplary scout image according to some embodiments of the present disclosure.

FIG. 6 is an exemplary scout image according to some embodiments of the present disclosure. The scout image was obtained by a pre-scanning performed on the head of a human subject. The scout image may include an ROI. For instance, the ROI may include the brain, the skull, the mandible, the nose, or the like, or a portion thereof, or any combination thereof. Merely by way of example, the pre-scanning for obtaining FIG. 6 is a CT scan. It should be noted that other types of pre-scanning may also be performed to obtain a scout image, such as PET scanning, MRI scanning.

Referring back to FIG. 5, in 504, the processing engine 140 (e.g., the segmentation module 420) may determine the ROI corresponding to the at least one portion of the subject. In some embodiments, the processing engine 140 may segment the scout image to determine the ROI in the scout image. For example, the processing engine 140 may segment the scout image using an image segmentation technique. The image segmentation technique may include but not limited to a threshold-based segmentation technique, a histogram-based segmentation technique, a template matching technique, a technique using a target segmentation model, or the like, or any combination thereof. In the following description, for illustration purposes, the target segmentation model may be used to segment the scout image, which is not intended to limit the scope of the present disclosure.

In some embodiments, the processing engine 140 may obtain the target segmentation model from a storage device (e.g., the storage device 150 described in FIG. 1). The target segmentation model may be used to segment the scout image to determine one or more regions in the scout image. In some embodiments, the target segmentation model may be a trained segmentation model. For instance, the target segmentation model may be a trained neural network model, such as a trained convolutional neural network (CNN) model, a fully convolutional network (FCN) model, a recurrent neural network (RNN) model, a V-net model, or the like.

In some embodiments, a plurality of trained segmentation models may be stored in the storage device. The plurality of trained segmentation models may correspond to various subjects (e.g., a human, a dog, a panda), various ROI of the subject (e.g., the head, the chest, the abdomen), and different numbers of regions to be generated by segmentation of the scout image (e.g., one region, two regions, three regions, or more). The processing engine 140 may select a target segmentation model from the plurality of trained segmentation models. Merely by way of example, the target segmentation model may correspond to the head of a patient, and the target segmentation model may be configured to segment the scout image to determine one region in the scout image that includes the brain (e.g., the ROI) of the human. In some embodiments, the processing engine 140 may input the scout image to the target segmentation model. The target segmentation model may segment the scout image to determine one or more regions in the scout image. For example, the processing engine 140 may use the target segmentation model to determine only one region in the scout image as the ROI of the subject. As another example, the target segmentation model may determine a plurality of regions as a plurality of ROIs of the subject. Each of the plurality of ROIs may include but not limited to a rib, an intervertebral disc, or the like. As yet another example, the target segmentation model may determine an ROI and one or more reference regions in the scout image. At least one scanning parameter (e.g., a scanning direction) may be determined based on the one or more reference regions.

In some embodiments, the target segmentation model may be trained according to a training process. Specifically, the processing engine 140 may obtain a segmentation model and a plurality of training samples. The target segmentation model may be obtained by training the segmentation model using the plurality of training samples. For instance, each of the plurality of training samples may include a sample scout image and a label associated with one or more sample regions segmented from the scout image. In some embodiments, the one or more sample regions may include only one sample ROI segmented from the scout image. In some embodiments, the one or more sample regions may include a plurality of sample ROIs segmented from the sample scout image. In some embodiments, the one or more sample regions may include a sample ROI and one or more sample reference regions associated with the sample ROI. For example, the one or more sample reference regions may include a sample reference ROI adjacent to the sample ROI. As another example, the one or more sample reference regions may include a first sample reference region and a second sample reference region. At least one of the first sample reference region or the second sample reference region may be adjacent to the sample ROI.

Figure 7A:
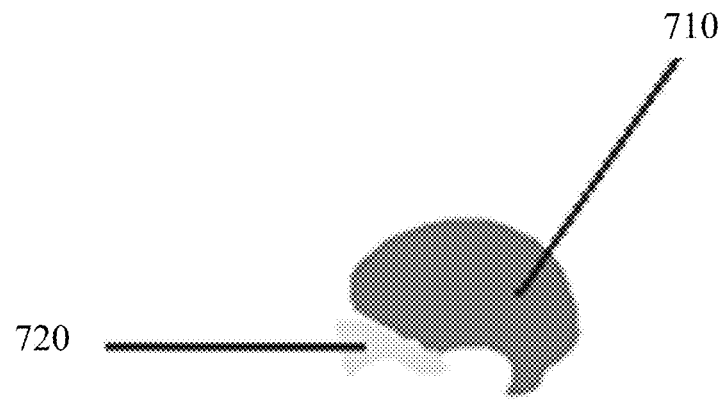
FIG. 7A is a schematic diagram illustrating an examplary sample ROI and an exemplary sample reference ROI segmented from a sample scout image according to some embodiments of the present disclosure.

FIG. 7A is a schematic diagram illustrating an examplary sample ROI and an exemplary sample reference ROI segmented from a sample scout image according to some embodiments of the present disclosure. For instance, the sample ROI 710 and the sample reference ROI 720 may be manually determined in a sample scout image by a user. The sample ROI 710 may correspond to the brain of a subject. The sample reference ROI 720 may be adjacent to the sample ROI 710. For example, the reference ROI 720 may include at least a portion of the orbit and at least a portion of the external acoustic meatus of the subject. An exemplary training sample may include the sample scout image and a label associated with the sample ROI 710 and the sample reference ROI 720.

Figure 7B:
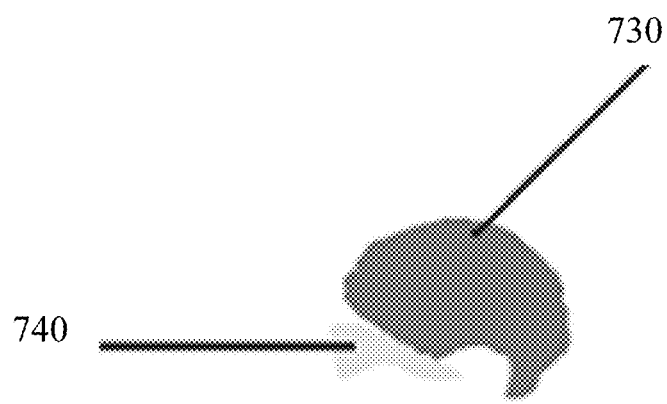
FIG. 7B is a schematic diagram illustrating an exemplary ROI and an exemplary reference ROI segmented from an exemplary scout image using a target segmentation model according to some embodiments of the present disclosure.

FIG. 7B is a schematic diagram illustrating an exemplary ROI and an exemplary reference ROI segmented from an exemplary scout image using a target segmentation model according to some embodiments of the present disclosure.

As illustrated in FIG. 7B, the ROI 730 may correspond to the brain of a subject. The reference ROI 740 may be adjacent to the ROI 730. For instance, the at least one scanning parameters may be determined based on the ROI 730 and the reference ROI 740.

Referring back to FIG. 5, in 506, the processing engine 140 (e.g., the determination module 430) may determine at least one scanning parameter associated with the at least one portion of the subject based on the ROI. In some embodiments, the at least one scanning parameter may include a scanning scope and/or a scanning direction. As used herein, the term "scanning scope" of a scan refers to a region that is scanned by the imaging device in the scan. Merely by way of example, during a scan, radiation beams (e.g., for a CT scanning) may be emitted toward a plurality of positions in the scanning scope. No radiation beams may be emitted toward a portion of the subject outside the scanning scope. For instance, for a helical CT scanning, the scanning scope may include a starting position and an ending position. The radioactive scanning source 115 may start emitting radiation rays when the radioactive scanning source 115 aligns with the staring position and stop emitting radiation rays when the radioactive scanning source 115 aligns with the ending position.

In some embodiments, the scanning direction may be determined for an axial scanning. As used herein, the term "scanning direction" may be a direction along which the radiation beams or the pulses or radio waves are emitted. In some embodiments, the scanning direction associated with the ROI may be parallel to a reference line associated with the ROI of the subject for the scanning by the imaging device. For example, the reference line associated with the head of the subject may include an orbitomeatal line, a glabellomeatal line, a Reid's base line, or the like. For a CT scan, the gantry (e.g., the gantry 111 of the imaging device 110) may be tilted by a certain angle (also referred to as a tilting angle) so that the radiation beams may be emitted toward the ROI along the scanning direction.

In some embodiments, the processing engine 140 may determine the scanning scope based on the contour of the ROI. For example, the processing engine 140 may determine a frame encompassing the ROI based on a plurality of points on the contour of the ROI. The frame may be a rectangle, a parallelogram, a trapezoid, or any other shape. Merely by way of example, the frame may be a bounding box encompassing the ROI. In some embodiments, the processing engine 140 may further adjust at least a portion of the frame to obtain an adjusted frame. For example, the processing engine 140 may increase or reduce the size of the frame through extending or shortening at least one side of the frame by an amount. In some embodiments, the amounts of the adjustment in at least two sides of a frame (e.g., a rectangular frame) may be the same or different. The adjusted frame may be designated as the scanning scope associated with the ROI, for example, for a helical scanning by the imaging device. More descriptions regarding the determination of the scanning scope based on the contour of the ROI may be found, for example, in FIG. 8 and the descriptions thereof.

In some embodiments, the processing engine 140 may determine the scanning direction associated with the ROI. The scanning scope associated with the ROI may be further determined based on a contour of the ROI and the scanning direction. Specifically, the processing engine 140 may determine a plurality of feature points (e.g., two or more feature points) on the contour of the ROI. A plurality of lines along the scanning directions may be determined. Each of the plurality of lines may pass through one of the plurality of feature points. The processing engine 140 may further determine a frame encompassing the ROI based on the plurality of lines. The scanning scope may be determined based on the frame. More descriptions regarding the determination of the scanning scope associated with the ROI based on the contour of the ROI and the scanning direction may be found elsewhere in the present disclosure, for example, in FIGS. 10, 13A, 13B, 14, and 15A and the descriptions thereof.

In some embodiments, the processing engine 140 may determine the scanning direction based on a second contour of each of the one or more reference regions. The scanning scope associated with the ROI may be further determined based on the scanning direction and the first contour of the ROI. For example, the one or more reference regions may include a first reference region (interchangeably referred to as a "reference ROI") adjacent to the ROI. The processing engine 140 may determine a plurality of reference feature points on the contour of the first reference region. The scanning direction may be determined based on the plurality of reference feature points on the contour of the first reference region. As another example, the one or more reference regions may include a first reference region and a second reference region. The processing engine 140 may determine the scanning direction based on the contour of the first reference region and the contour of the second reference region. More descriptions regarding the determination of the scanning direction based on the second contour of each of the one or more reference regions may be found elsewhere in the present disclosure, for example, in FIGS. 10-12 and 18-19 and the descriptions thereof. Additionally or alternatively, the processing engine 140 may determine the scanning direction based on the ROI. For instance, the processing engine 140 may determine one or more feature vectors associated with one or more features in the ROI. The feature vectors may be determined based on a covariance matrix indicating a difference between pixels in the ROI in the one or more features. More descriptions regarding the determination of the scanning direction based on the ROI may be found elsewhere in the present disclosure, for example, in FIGS. 14, 15A and 15B and the descriptions thereof.

A subsequent scanning based on the scout image may include an axial scanning, a helical scanning, or the like. For example, the axial scanning may include a sagittal scanning, a coronal scanning, and a transversal scanning. The subsequent scanning may be performed on the subject according to the at least one scanning parameters. In some embodiments, the processing engine 140 may reconstruct a two-dimensional (2D) or three-dimensional (3D) image based on the data obtained by the scanning. In some embodiments, the reconstructed 2D or 3D image may be transmitted to a storage device for storage.

It should be noted that the above description regarding the process 500 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations in the process 500 may be added or omitted. For example, after the at least one scanning parameter is determined, the processing engine 140 may evaluate the at least one scanning parameter and determine whether the at least one scanning parameter needs to be adjusted.

Figure 8:
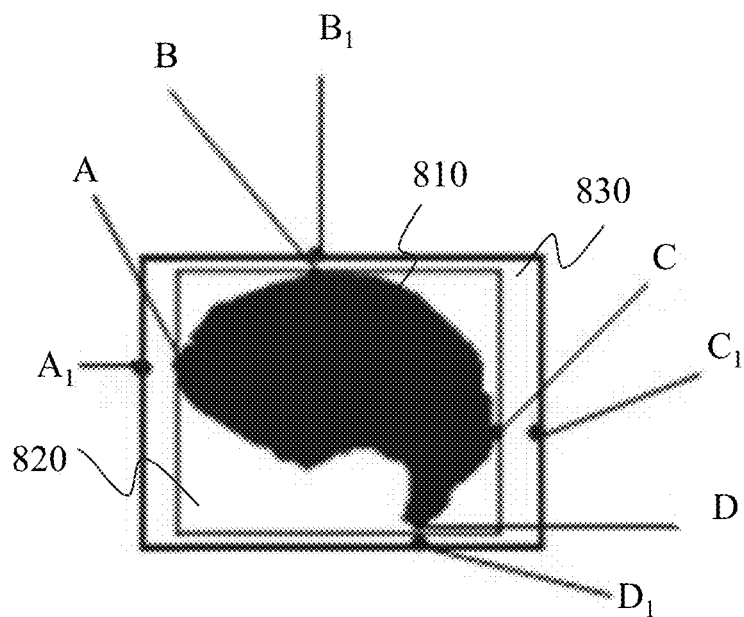
FIG. 8 is a schematic diagram illustrating an exemplary ROI, an exemplary frame, and an exemplary adjusted frame according to some embodiments of the present disclosure.

FIG. 8 is a schematic diagram illustrating an exemplary ROI, an exemplary frame, and an exemplary adjusted frame according to some embodiments of the present disclosure. For example, the processing engine 140 may determine a frame 820 based on the contour of the ROI 810, as illustrated in FIG. 8. The ROI 810 may correspond to the brain of a subject. The frame 820 may be a minimum parallelogram encompassing the ROI 810. Merely by way of example, the processing engine 140 may determine a first set of boundary points on the contour of the ROI 810. The frame 820 may be determined based on the first set of boundary points of the ROI 810. As used herein, a boundary point refers to a point on the contour of the ROI (e.g., the ROI 810) that is located farthest from a center of the ROI along a certain direction (e.g., a horizontal direction, a vertical direction). For example, as shown in FIG. 8, the first set of boundary points of the ROI 810 may include a left boundary point A, a top boundary point B, a right boundary point C, and a bottom boundary point D. The processing engine 140 may determine a minimum parallelogram based on the first set of boundary points. Specifically, the processing engine 140 may determine four lines. Each of the four lines may pass through one of the first set of boundary points of the ROI 810. The minimum parallelogram encompassing the ROI 810 may be determined based on the four lines. In some embodiments, the frame 820 may be a bounding box. As used herein, a bounding box refers to a minimum rectangle encompassing the ROI 810. For example, as shown in FIG. 8, a first line (e.g., a vertical line) may traverse the left boundary point A. A second line (e.g., a horizontal line) may traverse the top boundary point B. A third line (e.g., a vertical line) may traverse the right boundary point C. A fourth line (e.g., a horizontal line) may traverse the first bottom boundary point D. The frame 820 (e.g., a bounding box) may be formed by theses four lines.

In some embodiments, the processing engine 140 may further determine the adjusted frame 830 by adjusting the frame 820. The adjusted frame 830 may be obtained by increasing (extending) or reducing (shrinking) the size of the frame 820. For instance, the size of the frame 820 may be increased by extending one or more sides of the frame 820 (e.g., by extending one or more lines associated with the frame 820). In some embodiments, the extension of the frame 820 may be performed such that a contour region of the ROI 810 is also included in the adjusted frame 830. For example, the contour region may correspond to the skull of the subject. In some embodiments, at least two sides of the minimum parallelogram (i.e., the frame 820) may be extended by the same amount or different amounts. As used herein, the term "extend" refers to one or more sides of a frame are translated away from a central point of the ROI (e.g., the ROI 810) along a vertical direction or a horizontal direction, or one or more sides of the frame are elongated. For example, as illustrated in FIG. 8, the first line and the third line may be extended along the horizontal direction of the ROI. In some embodiments, the amount by which a line associated with the minimum parallelogram is extended may be pre-determined. For example, the four lines associated with the minimum parallelogram may be extended by the same amount, such as 1 centimeter (cm), 1.2 cm, 1.5 cm, etc. As another example, the first line associated with the minimum parallelogram may be extended by 1 cm; the second line associated with the minimum parallelogram may be extended by 1.2 cm; the third line associated with the minimum parallelogram may be extended by 1 cm; and the fourth line associated with the minimum parallelogram may be extended by 1.5 cm. In some embodiments, the processing engine 140 may reduce the size of the minimum parallelogram by translating at least one line associated with the minimum parallelogram along a vertical direction or a horizontal direction toward a central point of the ROI 810, or one or more sides of the frame are shortened. In some embodiments, a frame may be extended in one direction and shrunk in another direction.

In some embodiments, the processing engine 140 may determine a second set of boundary points based on the first set of boundary points. The second set of boundary points may be obtained by adjusting the one or more points of the first set of boundary points of the ROI 810. For example, the processing engine 140 may translate one or more points of the first set of boundary points away from the central point of the ROI 810 to determine the second set of boundary points. The adjusted frame 830 may be determined based on the second set of boundary points. For example, as illustrated in FIG. 8, the second set of boundary points may include an extended left boundary point $A_1$, an extended top boundary point $B_1$, an extended right boundary point $C_1$, and an extended right boundary point $D_1$. The processing engine 140 may determine four lines defining an adjusted frame 830 based on the second set of boundary points in a manner similar to the determination of the frame 820 based on the first set of boundary points.

In some embodiments, the amount(s) by which the one or more lines associated with the frame 820 are translated may be determined based on clinical applications. For instance, in the CT scanning, the contour region of the ROI (e.g., the ROI 810 shown in FIG. 8) may be a bone region or a portion thereof. The thickness of the bone region may vary for different subjects, different portions of the subject, etc. The amount by which a line associated with the minimum parallelogram is translated (herein also referred to as the translation distance) or changed (e.g., elongated or shortened) may be determined based on the thickness of the bone region. In some embodiments, the translation distance may be limited to protect important organs or tissue around the ROI from unnecessary radiation from the scanning. For example, if the ROI is located in a breast area, the at least one line associated with the minimum parallelogram may be extended for a shorter distance, as compared with the situation when ROI is located in the abdomen area. Additionally or alternatively, the size of the minimum parallelogram may be reduced. This may decrease radiation towards the heart.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the ROI may correspond to another portion of the subject, such as an intervertebral disc, a rib, a leg, an arm, a foot, or the like, or any combination thereof.

Figure 9:
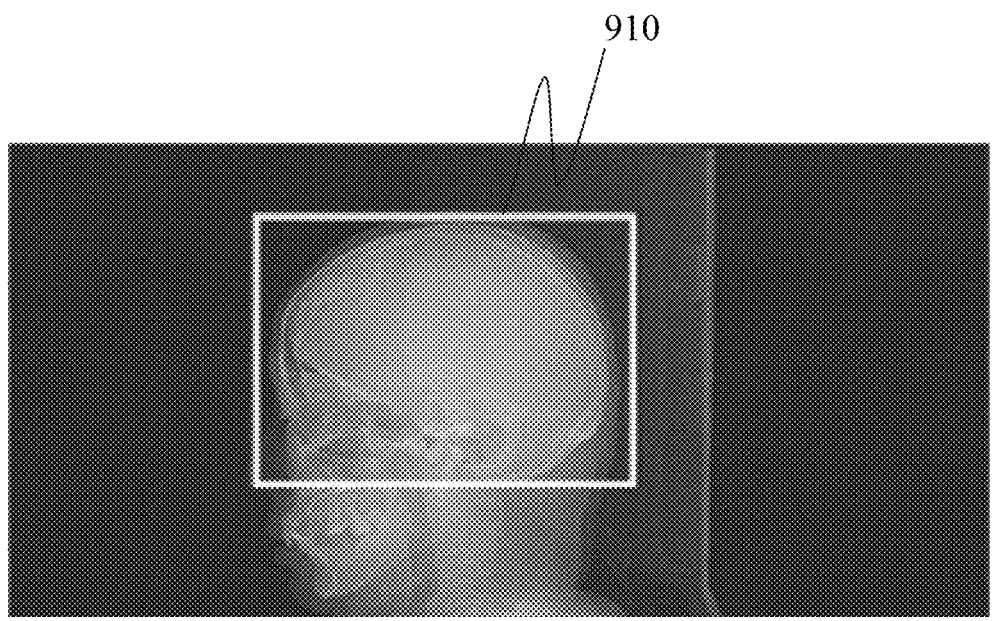
FIG. 9 is a schematic diagram illustrating an exemplary scanning scope for a helical scanning according to some embodiments of the present disclosure.

FIG. 9 is a schematic diagram illustrating an exemplary helical scanning scope for a helical scanning according to some embodiments of the present disclosure. Merely by way of example, the helical scanning scope 910 may correspond to the adjusted frame 830 in FIG. 8. As shown in FIG. 9, the helical scanning scope 910 includes the brain and the skull of the subject. A user may provide an instruction to the imaging device 110 to perform the scanning according to the scanning scope. For example, the imaging device 110 may perform a helical scanning from a starting position to an ending position defined by the helical scanning scope 910.

As shown in FIG. 9, the starting position may be associated with the top side of the helical scanning scope 910, and the ending position may be associated with the bottom side of the helical scanning scope 910. In some embodiments, the processing engine 140 may determine an axial scanning scope for the scanning of the imaging device 110 according to the process 1000 in FIG. 10, the process 1400 in FIG. 14, etc.

Figure 10:
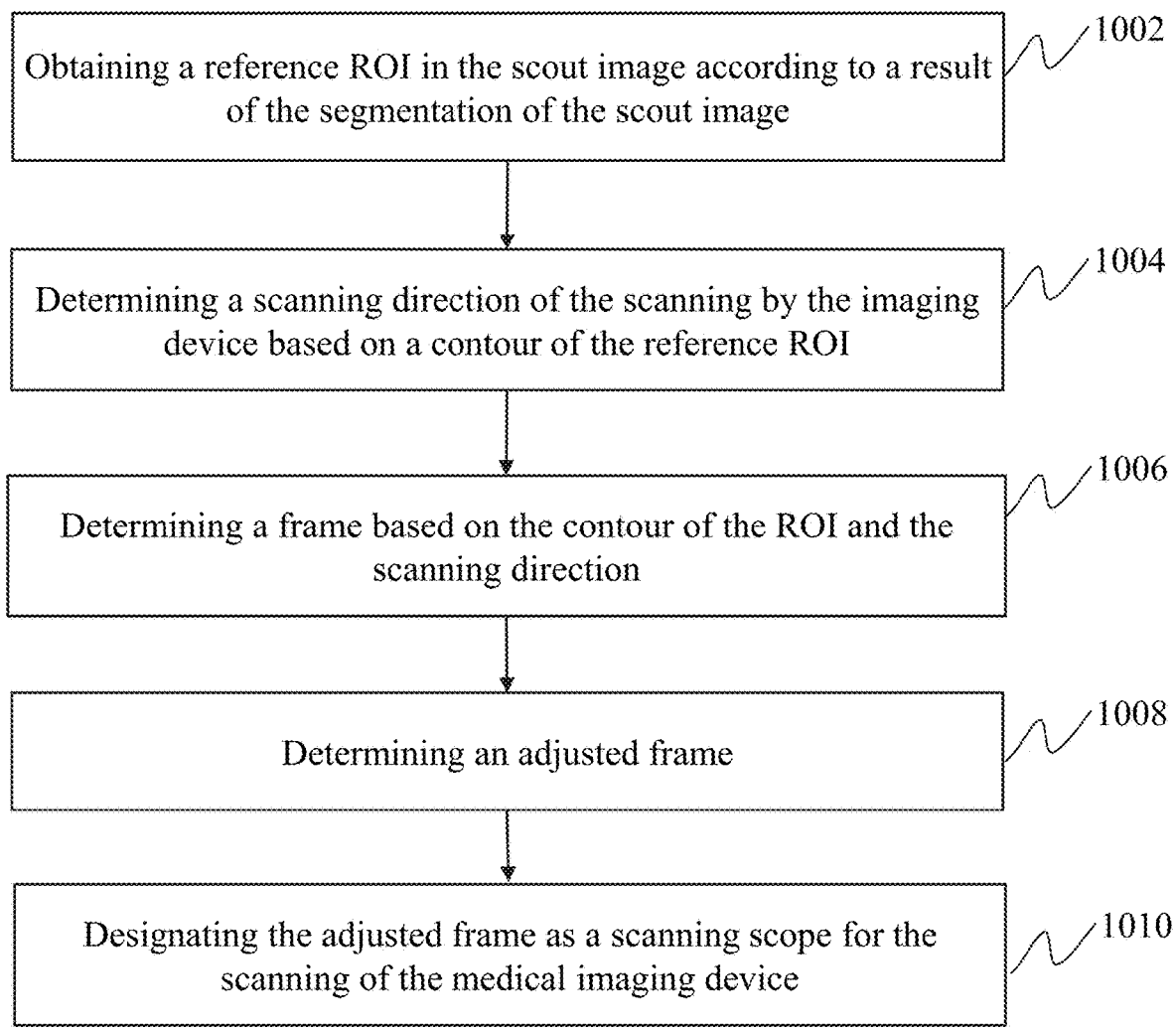
FIG. 10 is a flowchart illustrating an exemplary process for determining an axial scanning scope according to some embodiments of the present disclosure.

FIG. 10 is a flowchart illustrating an exemplary process for determining an axial scanning scope according to some embodiments of the present disclosure. In some embodiments, one or more operations of process 1000 illustrated in FIG. 10 may be implemented in the imaging system 100 illustrated in FIG. 1. For example, at least a part of the process 1000 illustrated in FIG. 10 may be stored in the storage device 150 in the form of instructions, and invoked and/or executed by the processing engine 140 (e.g., the processor 230 of the computing device 200 illustrated in FIG. 2, the GPU 330 or CPU 340 of the mobile device 300 illustrated in FIG. 3).

Figure 11:
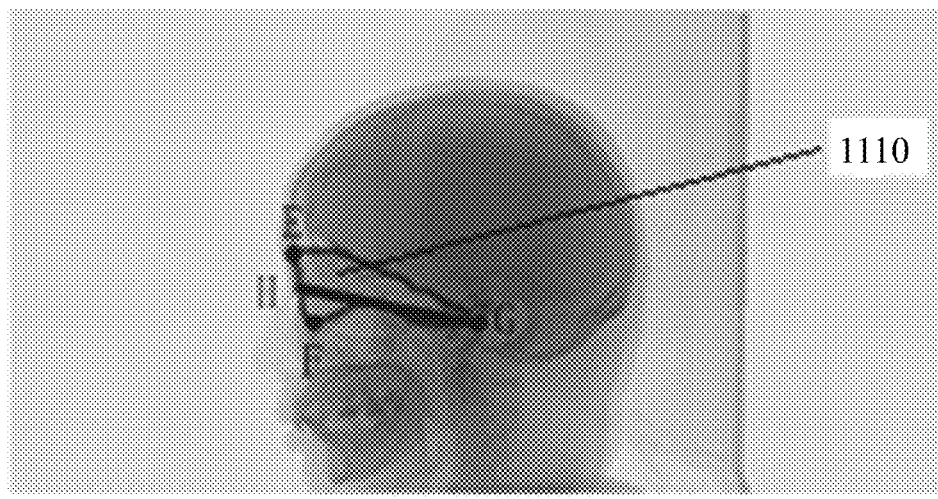
FIG. 11 is a schematic diagram illustrating an exemplary reference ROI according to some embodiments of the present disclosure.

In 1002, the processing engine 140 (e.g., the obtaining module 410) may obtain a reference ROI in the scout image according to a result of the segmentation of the scout image. In some embodiments, the reference ROI may be a region close to the ROI (e.g., the ROI 810 illustrated in FIG. 8). FIG. 11 is a schematic diagram illustrating an exemplary reference ROI according to some embodiments of the present disclosure. The reference ROI 1110 may include at least a portion of the orbit and at least a portion of the external acoustic meatus of the subject.

In 1004, the processing engine 140 (e.g., the determination module 430) may determine a scanning direction of the scanning by the imaging device (e.g., the imaging device 110) based on a contour of the reference ROI. In some embodiments, images obtained using different scanning directions may provide different diagnostic information. As shown in FIG. 11, the processing engine 140 may determine a plurality of reference feature points on the contour of the reference ROI 1110. In some embodiments, a reference line associated with the ROI may be determined based on the plurality of reference feature points. For instance, the reference line associated with at least a portion of the head of the subject may include an orbitomeatal line, a glabellomeatal line, a Reid's base line, or the like. In clinical applications, the scanning direction may be parallel to the reference line associated with the ROI. The reference line may pass through one or more feature parts of the subject. For instance, the orbitomeatal line passes through the nasion and the external acoustic meatus of the subject. As another example, the glabellomeatal line passes through the glabella and the external acoustic meatus of the subject.

Figure 12:
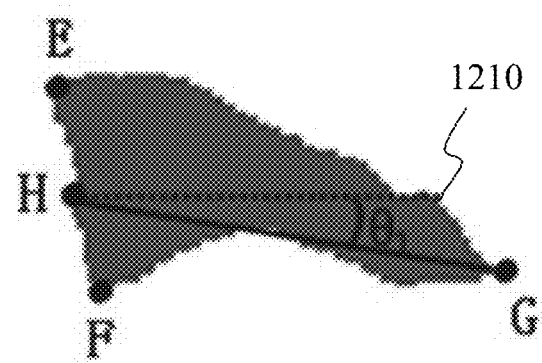
FIG. 12 is an enlarged view of the reference ROI in FIG. 11 according to some embodiments of the present disclosure.

Merely by way of example, the reference line may be the orbitomeatal line. As illustrated in FIG. 11, the plurality of reference feature points may include a vertex E on the top left of the reference ROI 1110, a vertex F on the bottom left of the reference ROI 1110, and a vertex G on the right of the reference ROI 1110. The vertex G may correspond to the external acoustic meatus of the subject. A line segment EF may be determined based on the vertex E and the vertex F. A midpoint H of the line segment EF may be determined. A line segment HG may be determined based on the midpoint H (e.g., corresponding to the nasion of the subject) and the vertex G on the right of the reference ROI 1110. The processing engine 140 may designate a direction along the line segment HG as the scanning direction. FIG. 12 is an enlarged view of the reference ROI 1110 in FIG. 11. A first angle $\theta_1$ between the line segment HG and a horizontal line of the reference ROI 1110 (illustrated as a dashed line 1210 in FIG. 12) may be determined. In some embodiments, the processing engine 140 may transmit the first angle $\theta_1$ to the imaging device 110 as a controlling parameter associated with the scanning direction. For instance, the first angle may be designated as the tilting angle of the gantry of a CT scanner.

Referring back to FIG. 10, in 1006, the processing engine 140 (e.g., the determination module 430) may determine a frame based on the contour of the ROI and the scanning direction. In some embodiments, the processing engine 140 may determine a plurality of feature points on the contour of the ROI. Specifically, the plurality of feature points on the contour of the ROI may be determined based on the scanning direction.

Figure 13A:
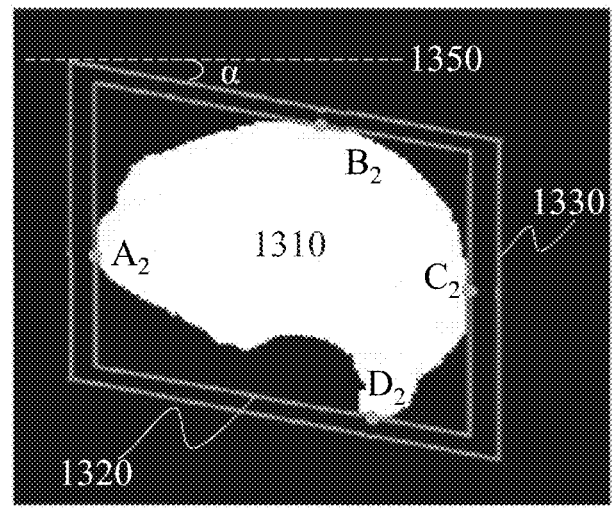
FIG. 13A is a schematic diagram illustrating an exemplary ROI, an exemplary frame, and an exemplary adjusted frame according to some embodiments of the present disclosure.

FIG. 13A is a schematic diagram illustrating an exemplary ROI, an exemplary frame, and an exemplary adjusted frame according to some embodiments of the present disclosure. Merely by way of example, the processing engine 140 may determine a plurality of feature points on the contour of an ROI 1310 shown in FIG. 13A. The plurality of feature points of the ROI 1310 may include a left feature point $A_2$, a top feature point $B_2$, a right feature point $C_2$, and a bottom feature point $D_2$. Merely by way of example, the top feature point $B_2$ may be a top boundary point along a feature direction that is perpendicular to the scanning direction. The bottom feature point $D_2$ may be a bottom boundary point along the feature direction. Additionally or alternatively, the left feature point $A_2$ may be a boundary point along the left direction in FIG. 13A, and the right feature point $C_2$ may be a boundary point along the right direction in FIG. 13A. The processing engine 140 may generate four lines. Each of the four lines may pass through one of the plurality of feature points. The four lines may form a minimum parallelogram (e.g., the frame 1320) encompassing the ROI 1310. For example, a fifth line may be a vertical line traversing the left feature point $A_2$. A sixth line may be a line that traverses the top feature point $B_2$ and aligns with the scanning direction. An angle α between the sixth line and a horizontal direction (illustrated as a dashed line 1350) in the FIG. 13A is equal to the first angle $\theta_1$ associated with the scanning direction. A seventh line may be a vertical line traversing the right feature point $C_2$. An eighth line may be a line that traverses the bottom feature point $D_2$. An angle between the eighth line and a horizontal direction is equal to the first angle $\theta_1$ associated with the scanning direction. The frame 1320 shown in FIG. 13A may be determined by the four lines described above (i.e., the fifth line, the sixth line, the seventh line, and the eighth line).

In 1008, the processing engine 140 (e.g., the determination module 430) may determine an adjusted frame. For example, the processing engine 140 may determine the adjusted frame by increasing or reducing the size of the frame. Specially, the processing engine 140 may increase the size of the frame by extending one or more lines associated with the frame. The one or more lines associated with the frame may be extended by the same amount or different amounts. Operation 1008 may be performed similarly as described earlier in FIG. 8. The adjusted frame 1330 is shown in FIG. 13A.

Figure 13B:
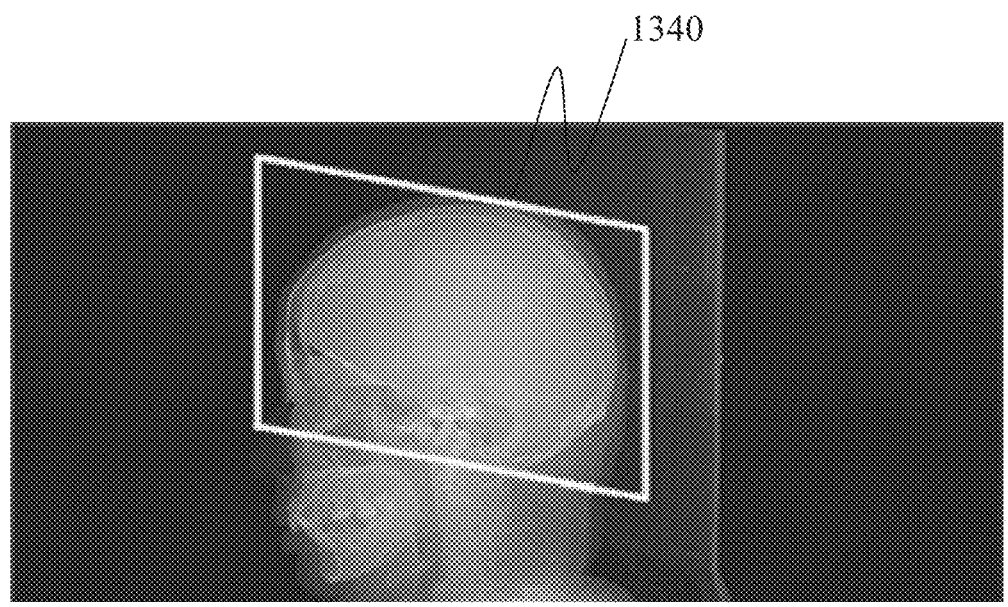
FIG. 13B is a schematic diagram illustrating an exemplary axial scanning scope according to some embodiments of the present disclosure.

In 1010, the processing engine 140 (e.g., the determination module 430) may designate the adjusted frame as a scanning scope for the scanning of the imaging device 110. FIG. 13B is a schematic diagram illustrating an exemplary axial scanning scope according to some embodiments of the present disclosure. The axial scanning scope 1340 may correspond to the adjusted frame 1330 shown in FIG. 13A.

The imaging device 110 may perform an axial scanning according to the axial scanning scope 1340.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 14:
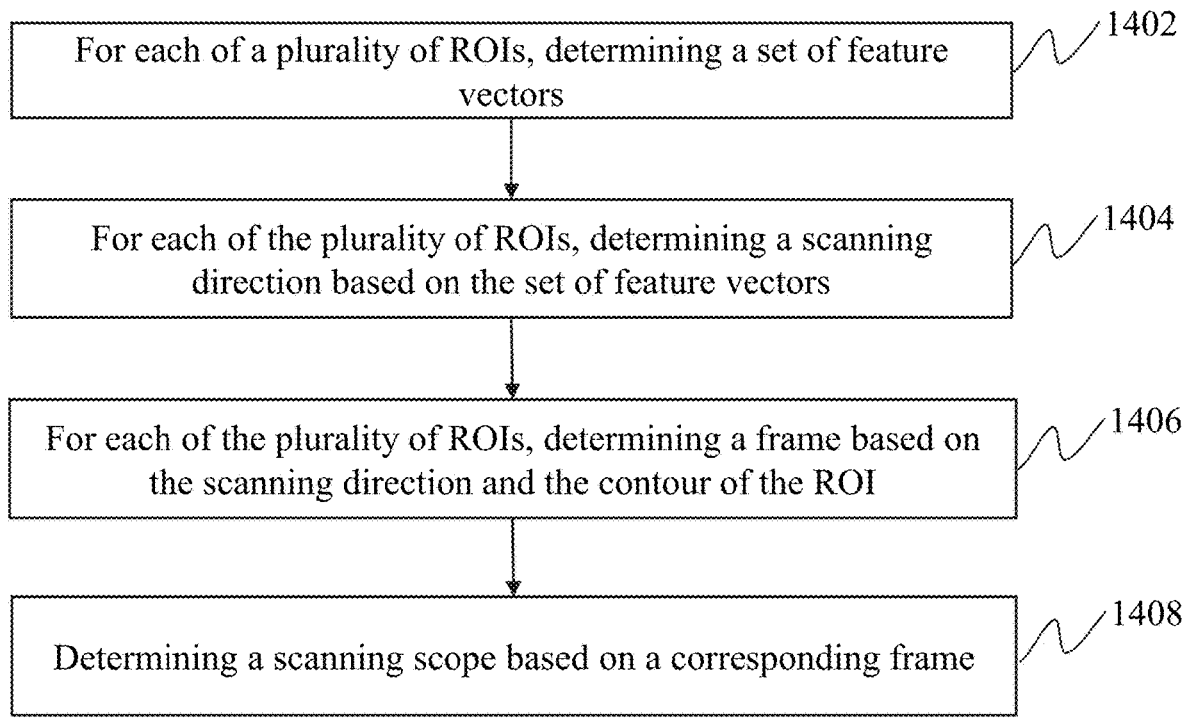
FIG. 14 is a flowchart illustrating an exemplary process for determining an axial scanning scope according to some embodiments of the present disclosure.

FIG. 14 is a flowchart illustrating an exemplary process for determining an axial scanning scope according to some embodiments of the present disclosure. In some embodiments, one or more operations of the process 1400 illustrated in FIG. 14 may be implemented in the imaging system 100 illustrated in FIG. 1. For example, at least a part of the process 1400 illustrated in FIG. 14 may be stored in the storage device 150 in the form of instructions, and invoked and/or executed by the processing engine 140 (e.g., the processor 230 of the computing device 200 illustrated in FIG. 2, the GPU 330 or CPU 340 of the mobile device 300 illustrated in FIG. 3). In some embodiments, the processing engine 140 may determine a plurality of ROIs in the scout image. For each of the plurality of ROIs, the processing engine 140 may determine a scanning scope associated with the ROI for a scanning by an imaging device. For example, the scanning may be an MRI scanning, a CT scanning, a PET scanning, etc.

Figure 15A:
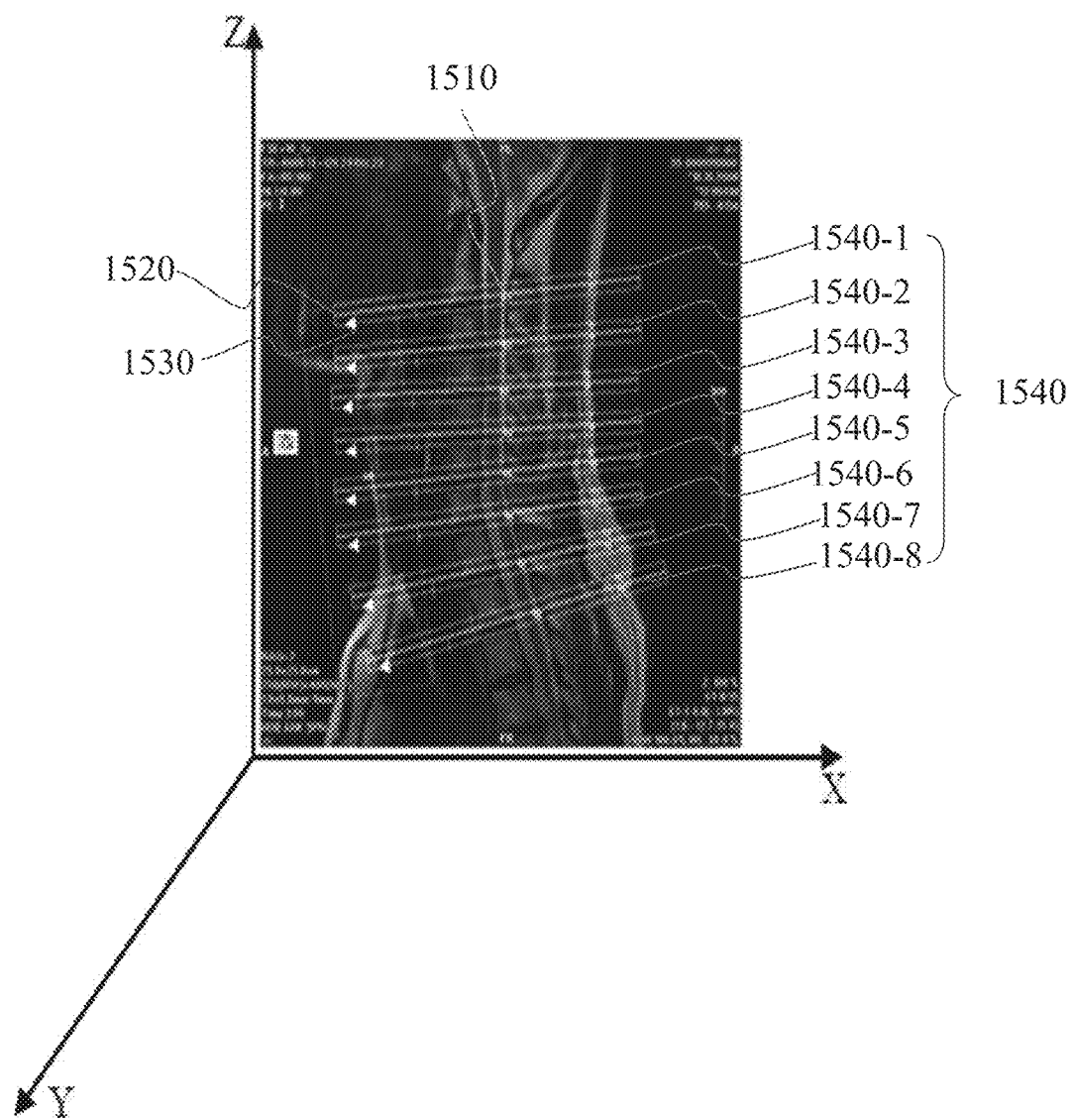
FIG. 15A is a schematic diagram of determining a plurality of scanning scopes for a plurality of ROIs according to some embodiments of the present disclosure.
Figure 15B:
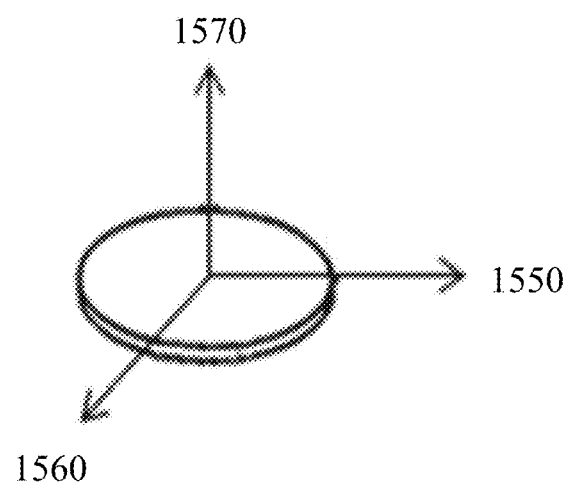
FIG. 15B is a schematic diagram of three principal directions according to some embodiments of the present disclosure.

In 1402, for each of a plurality of ROIs, the processing engine 140 may determine a set of feature vectors. For example, the plurality of ROIs may be the intervertebral disks shown in FIG. 15A. In some embodiments, the processing engine 140 may determine a 3D coordinate system. For example, as shown in FIG. 15A, a first axis may be a horizontal axis (illustrated as the X-axis). The first axis and a second axis may form a plane. For instance, the second axis may be perpendicular to the first axis (illustrated as the Y-axis). A third axis may be oblique or perpendicular to the plane formed by the first axis and the second axis. For instance, the third axis may be a vertical axis (illustrated as the Z-axis) that is perpendicular to the plane formed by the first axis and the second axis. In some embodiments, the coordinates of pixels in each of the plurality of ROIs may be determined according to the 3D coordinate system. In some embodiments, for each of the plurality of ROIs, the processing engine 140 may determine a covariance matrix based on the coordinates of the pixels in the ROI. The covariance matrix may indicate a difference between pixels in the ROI in the one or more features (e.g., pixel coordinates). Eigenvalues and one or more feature vectors may be determined based on the covariance matrix. In some embodiments, the set of feature vectors for the ROI may be determined by selecting three feature vectors corresponding to top three highest eigenvalues.

Figure 16:
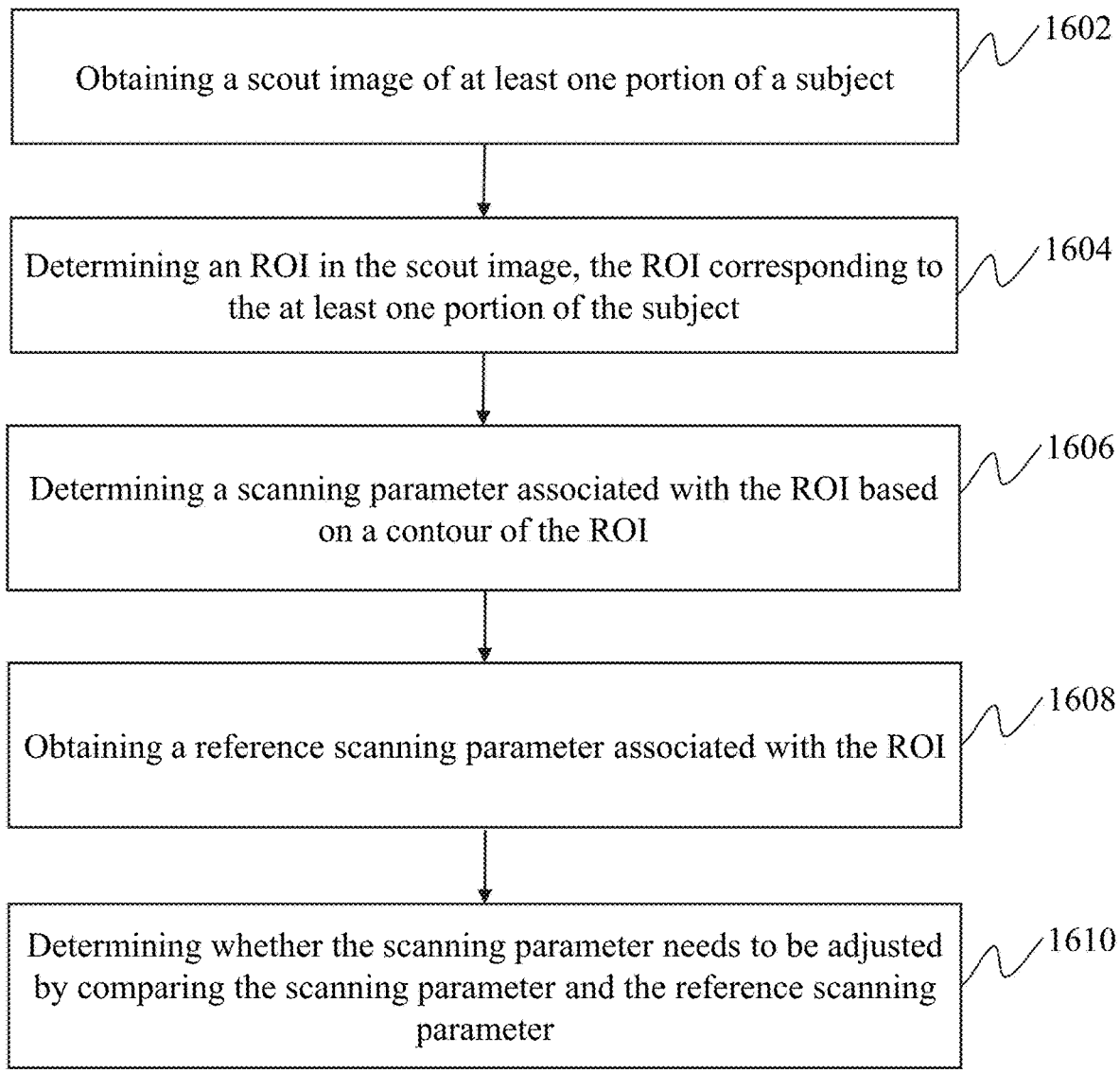
FIG. 16 is a flowchart illustrating an exemplary process for evaluating a scanning parameter according to some embodiments of the present disclosure.

In 1404, for each of the plurality of ROIs, the processing engine 140 may determine a scanning direction based on the set of feature vectors. In some embodiments, the three feature vectors may correspond to three candidate directions for three principal directions. The processing engine 140 may compare angles between each of the three candidate directions and the X direction, angles between each of the three candidate directions and the Y direction, and angles between each of the three candidate directions and the Z direction. A candidate direction that forms the smallest angle with the X direction may be designated as a first principal direction (as illustrated by a first principal direction 1550 in FIG. 15B). A candidate direction that forms the smallest angle with the Y direction may be designated as a second principal direction (as illustrated by a second principal direction 1560 in FIG. 15B). A candidate direction that forms the smallest angle with the Z direction may be designated as a third principal direction (as illustrated by a third principal direction 1570 in FIG. 15B). The first principal direction 1550 may be designated as the scanning direction. For example, the scanning direction 1630 is shown in FIG. 16.

In 1406, for each of the plurality of ROIs, the processing engine 140 may determine a frame based on the scanning direction and the contour of the ROI. For example, the processing engine 140 may determine the frame based on the scanning direction and the contour of the ROI according to operations 1006 to 1010 described in connection with FIG. 10. In some embodiments, the processing engine 140 may determine the center of gravity of the ROI. FIG. 15A is a schematic diagram of determining a plurality of scanning scopes for a plurality of ROIs according to some embodiments of the present disclosure. Merely by way of example, the ROI may include an intervertebral disk illustrated in FIG. 15A. In some embodiments, the processing engine 140 may determine a frame (e.g., a minimum parallelogram) that encompasses the ROI. For instance, the frame may be a rectangle. As illustrated in FIG. 15A, a plurality of frames 1540 (e.g., 1540-1, 1540-2, . . . , 1540-8) associated with a plurality of ROIs may be determined.

In 1408, the processing engine 140 may determine a scanning scope based on a corresponding frame. For instance, the imaging device 110 may perform a scanning based on an axial scanning scope corresponding to an intervertebral disk region according to the frame 1540. In some embodiments, the imaging device 110 may obtain a plurality of axial images that are parallel to a scanning plane. For instance, as shown in FIG. 15A, the scanning plane 1520 may be perpendicular to the third principal direction 1570 and may traverse a center of gravity 1510 of the ROI. The processing engine 140 may determine the center of gravity 1510 based on geometric features of the ROI.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

FIG. 16 is a flowchart illustrating an exemplary process for evaluating a scanning parameter according to some embodiments of the present disclosure. In some embodiments, one or more operations of the process 1600 illustrated in FIG. 16 may be implemented in the imaging system 100 illustrated in FIG. 1. For example, at least a part of the process 1600 illustrated in FIG. 16 may be stored in the storage device 150 in the form of instructions, and invoked and/or executed by the processing engine 140 (e.g., the processor 230 of the computing device 200 illustrated in FIG. 2, the GPU 330 or CPU 340 of the mobile device 300 illustrated in FIG. 3). In some embodiments, operation 1602 and operation 1604 may be performed in a manner similar to operation 502 and operation 504 in FIG. 5.

In 1602, the processing engine 140 (e.g., the obtaining module 410) may obtain a scout image of at least one portion of a subject.

In 1604, the processing engine 140 (e.g., the segmentation module 410) may determine an ROI in the scout image, the ROI corresponding to the at least one portion of the subject.

In 1606, the processing engine 140 (e.g., the determination module 430) may determine a scanning parameter associated with the ROI based on a contour of the ROI. The scanning parameter may include a scanning direction, a scanning scope, or the like, or any combination thereof. In some embodiments, the scanning scope may further include a starting location and an ending location. In some embodiments, the processing engine 140 may determine the scanning parameter according to a first operation. For example, the first operation may include determining a first reference region adjacent to the ROI using a target segmentation model, and determining the scanning direction associated with the ROI based on the first reference region. As another example, the first operation may include determine the scanning scope associated with the ROI based on the scanning direction and the contour of the ROI.

In 1608, the processing engine 140 (e.g., the obtaining module 410) may obtain a reference scanning parameter associated with the ROI. In some embodiments, the reference scanning parameter may be determined according to a second operation. At least a portion of the second operation may be different from the first operation. For example, the second operation may include using a target segmentation model to determine a first reference region adjacent to the ROI and a second reference region adjacent to the first reference region. The second operation may further include determining a reference scanning direction based on the contour of the first reference region. As another example, the second operation may include determining one or more feature vectors based on the ROI, and determining the reference scanning direction based on the one or more feature vectors.

In 1610, the processing engine 140 (e.g., the determination module 430) may determine whether the scanning parameter needs to be adjusted by comparing the scanning parameter and the reference scanning parameter. In some embodiments, the processing engine 140 may determine a difference between the scanning parameter and the reference scanning parameter. For example, the processing engine 140 may further determine a reliability factor of the scanning parameter based on the difference between the scanning parameter and the reference scanning parameter. For example, the reliability factor may have a value between 0 to 1. In some embodiments, the processing engine 140 may compare the reliability factor with a threshold. In response to a determination that the reliability factor is less than the threshold, the processing engine 140 may determine that the scanning parameter needs to be adjusted. An edit option may be provided to the user to modify the scanning parameter. More descriptions regarding the evaluation of the at least one scanning parameter may be found elsewhere in the present disclosure, for example, in FIG. 17 and the descriptions thereof.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 17:
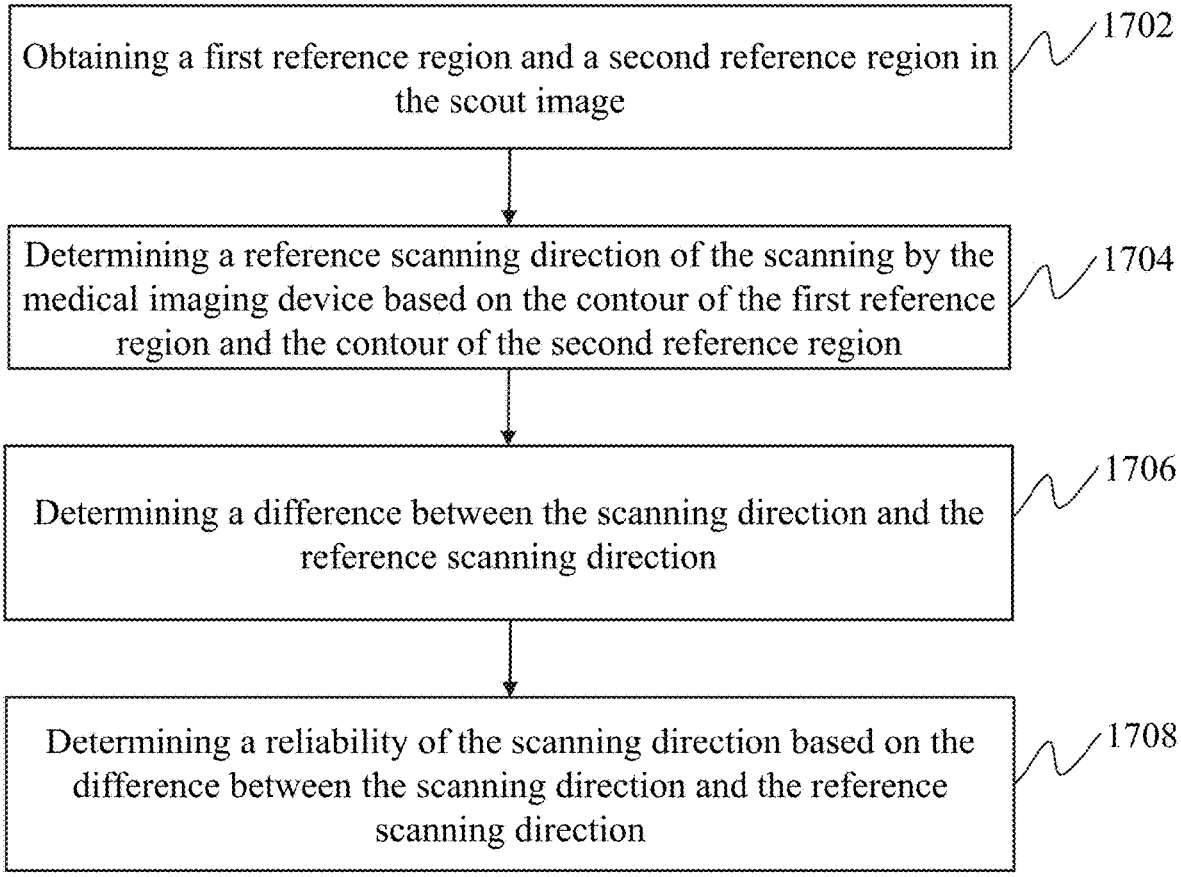
FIG. 17 is a flowchart illustrating an exemplary process for determining a reliability factor of the scanning direction according to some embodiments of the present disclosure.

FIG. 17 is a flowchart illustrating an exemplary process for determining the reliability factor of the scanning direction according to some embodiments of the present disclosure. In some embodiments, one or more operations of the process 1700 illustrated in FIG. 17 may be implemented in the imaging system 100 illustrated in FIG. 1. For example, at least a part of the process 1700 illustrated in FIG. 17 may be stored in the storage device 150 in the form of instructions, and invoked and/or executed by the processing engine 140 (e.g., the processor 230 of the computing device 200 illustrated in FIG. 2, the GPU 330 or CPU 340 of the mobile device 300 illustrated in FIG. 3).

Figure 18:
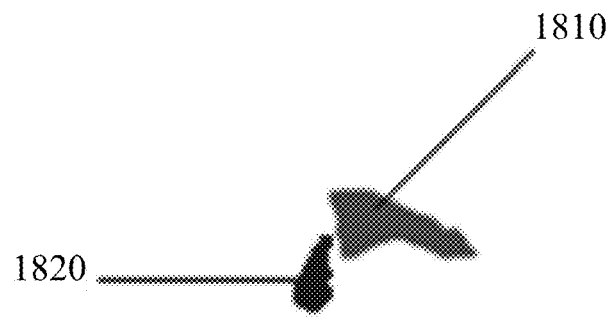
FIG. 18 is a schematic diagram illustrating an exemplary first reference region and an exemplary second reference region according to some embodiments of the present disclosure.

In 1702, the processing engine 140 may obtain a first reference region and a second reference region in the scout image. In some embodiments, the first reference region may be adjacent to the ROI, and the second reference region may be adjacent to the first reference region. For example, as shown in FIG. 18, the first reference region 1810 may include at least a portion of the orbit and at least a portion of the external acoustic meatus of the subject. The second reference region 1820 may correspond to a nose area.

In 1704, the processing engine 140 may determine a reference scanning direction of the scanning by the imaging device based on the contour of the first reference region and the contour of the second reference region. In some embodiments, the processing engine 140 may determine a first point on the contour of the second reference region. The processing engine 140 may determine a second point on the contour of the first reference region based on the first point on the second contour of the second reference region. The second point may be an intersection point of the contour of the first reference region and a feature line (e.g., a horizontal line) passing through the first point. The processing engine 140 may further determine the reference scanning direction based on the second point and a third point on the contour of the first reference region.

Figure 19:
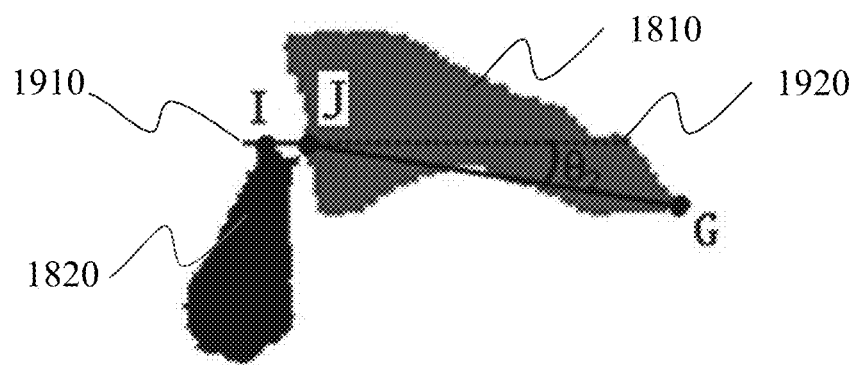
FIG. 19 is a schematic diagram of determining a reference scanning direction according to some embodiments of the present disclosure.

For example, as illustrated in FIG. 19, the processing engine 140 may designate a vertex G on the right of the first reference region 1810 as the third point on the contour of the first reference region 1810. A top boundary point I may be designated as a first point of the second reference region 1820. A horizontal line 1910 (i.e., a feature line) that traverses the first point I may intersect with the first reference region 1810 at the second point J on the contour of the first reference region 1810. A line segment JG may be determined based on the third point G and the second point J. The reference scanning direction may be parallel to the line segment JG. In some embodiments, an angle between the scanning direction and a horizontal direction may be denoted as $\theta_1$. A reference angle between the reference direction and a horizontal direction may be denoted as $\theta_2$. In some embodiments, the processing engine 140 may designate an angle between the line segment JG and a horizontal direction (illustrated as a dashed line 1920 in FIG. 19) as a reference angle $\theta_2$. The angle $\theta_1$ and the reference angle $\theta_2$ may be used to determine the reliability factor associated with the scanning direction as described in operation 1708.

In 1706, the processing engine 140 may determine a difference between the scanning direction and the reference scanning direction. For example, a difference between $\theta_1$ and $\theta_2$ may be used to represent the difference between the scanning direction and the reference scanning direction. Specifically, the difference between the scanning direction and the reference scanning direction may be determined as $|\theta_1-\theta_2|$, which refers to the absolute value of the difference between $\theta_1$ and $\theta_2$.

In 1708, the processing engine 140 may determine the reliability factor of the scanning direction based on the difference between the scanning direction and the reference scanning direction. The reliability factor of the scanning direction may relate to the reliability factor of the axial scanning scope. In some embodiments, the reliability factor of the scanning direction may be evaluated using one or more pre-determined parameters and the difference between the scanning direction and the reference scanning direction.

For example, the reliability factor of the scanning direction may be determined according to Equation (1):

$$M = 1.0 - \frac{|\theta_1 - \theta_2|}{\theta_0}, \quad (1)$$

where M refers to the reliability factor of the scanning direction, and $\theta_0$ refers to a pre-set reference error value of the scanning direction. In some embodiments, $\theta_0$ is determined according to the specific area to be scanned. For instance, when an area closes to the ROI to be scanned includes important organs or tissues that should be protected against unnecessary radiation, $\theta_0$ may be adjusted. Merely by way of example, if an axial scanning is to be performed on the head of the subject, $\theta_0$ may be 15 degrees. If the axial scanning is performed on the breast of the subject, $\theta_0$ may be 10 degrees so as to prevent or reduce unnecessary radiation to the heart area.

In some embodiments, the processing engine 140 or a user may determine whether to modify the scanning direction based on the reliability factor of the scanning direction (i.e., M). The processing engine 140 may provide an edit option for the user to modify the axial scanning scope when necessary. For example, the processing engine 140 may compare M with a pre-set first threshold $T_1$ and a pre-set second threshold $T_2$. If $T_1 \leq M \leq 1$, the scanning direction may be determined as reliable and does not need to be modified. The processing engine 140 may automatically send an instruction to direct the imaging device 110 to perform the axial scanning. Alternatively, the user may be asked to confirm the scanning scope and send an instruction to cause the imaging device 110 to start the axial scanning. If $T_2 \leq M < T_1$, there may be a slight error in the scanning direction. In some embodiments, the processing engine 140 may send a first notification message to inform the user that a slight modification may be needed for the scanning direction. The user may modify the axial scanning scope according to the notification. If $M < T_2$, there may be a significant error in the determination result of the scanning direction. In some embodiments, the processing engine 140 may send a second notification message to inform the user that a significant modification to the scanning scope may be needed. The user may modify the axial scanning scope according to the notification. For example, the user may view the axial scanning scope and make modifications via the terminal 130, through operations such as translating, rotating, enlarging, or reducing the axial scanning scope, or the like, or any combination thereof. The processing engine 140 or the user may send an instruction to direct the imaging device 110 to perform the axial scanning according to the modified axial scanning scope. Merely by way of example, the first threshold $T_1$ may be 0.8 and the second threshold $T_2$ may be 0.6. As another example, the first threshold $T_1$ may be 0.7, and the second threshold $T_2$ may be 0.5.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the reference scanning direction may be determined by other means. For example, the reference scanning direction may be determined based on a plurality of feature vectors in a manner similar to operation 1404.

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB.

NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

We claim:

1. A method for determining at least one scanning parameter for a scanning by an imaging device, implemented on a machine having at least one processor and a storage device, the method comprising:
    obtaining a scout image of at least one portion of a subject;
    determining, in the scout image, a region of interest (ROI) corresponding to the at least one portion of the subject; and
    determining, based on the ROI, the at least one scanning parameter associated with the at least one portion of the subject for performing the scanning by the imaging device, the at least one scanning parameter including a scanning direction of an axial scanning, wherein the determining, based on the ROI, the at least one scanning parameter, includes:
        determining, based on coordinates of pixels in the ROI, a covariance matrix, the covariance matrix indicating a difference between pixels in the ROI in multiple pixel coordinates;
        determining, based on the covariance matrix, one or more feature vectors associated with the multiple pixel coordinates;
        determining, three feature vectors corresponding to top three highest eigenvalues in the multiple feature vectors, the three feature vectors corresponding to three candidate directions; and
        determining, from the three candidate directions, a candidate direction as the scanning direction, the candidate direction forming a smallest angle with a horizontal axis direction among the three candidate directions.

2. The method of claim 1, wherein the determining an ROI from the scout image includes:
    segmenting the scout image using a target segmentation model.

3. The method of claim 2, wherein the target segmentation model is a trained neural network model.

4. The method of claim 2, wherein the target segmentation model is trained according to a training process, the training process comprising:
    obtaining a plurality of training samples, each of the plurality of training samples including a sample scout image and a label associated with one or more sample regions segmented from the sample scout image; and
    using the plurality of training samples to obtain the target segmentation model.

5. The method of claim 1, wherein the at least one scanning parameter includes a scanning scope, and wherein the determining, based on the ROI, the at least one scanning parameter, further includes:
    determining, based on a contour of the ROI, a frame encompassing the ROI; and
    determining, based on the frame, the scanning scope associated with the ROI.

6. The method of claim 5, wherein the determining, based on a contour of the ROI, a frame encompassing the ROI, includes:
    generating, based on a plurality of points on the contour of the ROI, the frame encompassing the ROI.

7. The method of claim 6, wherein the frame forms a minimum parallelogram encompassing the ROI and the determining, based on the frame, the scanning scope associated with the ROI includes:
    determining, based on a thickness of a bone region of the subject, a translation distance of at least a portion of the frame;
    obtaining an adjusted frame by adjusting at least a portion of the frame based on the translation distance; and
    designating the adjusted frame as the scanning scope associated with the ROI.

8. The method of claim 1, wherein the at least one scanning parameter further includes a scanning scope, and wherein the determining, based on the ROI, the at least one scanning parameter, further includes:
    determining, based on the scanning direction and a contour of the ROI, the scanning scope associated with the ROI.

9. The method of claim 8, wherein the determining, based on the scanning direction and a contour of the ROI, the scanning scope associated with the ROI, includes:
    determining, based on the scanning direction, a plurality of feature points on the contour of the ROI;
    determining a plurality of lines along the scanning direction, each of the plurality of lines passing through one of the plurality of feature points on the contour of the ROI; and
    determining, based on the plurality of lines, a frame encompassing the ROI as the scanning scope associated with the ROI.

10. The method of claim 1, further comprising:
obtaining a reference scanning parameter for each of the at least one scanning parameter associated with the ROI; and
determining whether a scanning parameter of the at least one scanning parameter needs to be adjusted by comparing the scanning parameter with the corresponding reference scanning parameter.

11. The method of claim 1, wherein the scanning direction defines a tilting angle of a gantry of the imaging device or a direction along which the radiation beams or the pulses or radio waves are emitted.

12. A system for determining at least one scanning parameter for a scanning by an imaging device, comprising:
at least one non-transitory storage medium including a set of instructions; and
at least one processor in communication with the at least one non-transitory storage medium, wherein when executing the set of instructions, the at least one processor is configured to cause the system to:
obtain a scout image of at least one portion of a subject;
determine, in the scout image, a region of interest (ROI) corresponding to the at least one portion of the subject; and
determine, based on the ROI, the at least one scanning parameter associated with the at least one portion of the subject for performing the scanning by the imaging device, the at least one scanning parameter including a scanning direction of an axial scanning, wherein the determining, based on the ROI, the at least one scanning parameter, includes:
determining, based on coordinates of pixels in the ROI, a covariance matrix, the covariance matrix indicating a difference between pixels in the ROI in multiple pixel coordinates;
determining, based on the covariance matrix, one or more feature vectors associated with the multiple pixel coordinates;
determining, three feature vectors corresponding to top three highest eigenvalues in the multiple feature vectors, the three feature vectors corresponding to three candidate directions; and
determining, from the three candidate directions, a candidate direction as the scanning direction, the candidate direction forming a smallest angle with a horizontal axis direction among the three candidate directions.

13. The system of claim 12, wherein the at least one scanning parameter includes a scanning scope, and wherein the determining, based on the ROI, the at least one scanning parameter, further includes:
determining, based on a contour of the ROI, a frame encompassing the ROI; and
determining, based on the frame, the scanning scope associated with the ROI.

14. The system of claim 13, wherein the determining, based on a contour of the ROI, a frame encompassing the ROI, includes:
generating, based on a plurality of points on the contour of the ROI, the frame encompassing the ROI.

15. The system of claim 14, wherein the determining, based on the frame, the scanning scope associated with the ROI includes:
obtaining an adjusted frame by adjusting at least a portion of the frame; and
designating the adjusted frame as the scanning scope associated with the ROI.

16. A method for evaluating a scanning parameter, implemented on a machine having at least one processor and a storage device, the method comprising:
obtaining a scout image of at least one portion of a subject;
determining, in the scout image, a region of interest (ROI) corresponding to the at least one portion of the subject;
determining, based on a contour of the ROI, a scanning parameter associated with the ROI, the scanning parameter including a scanning direction;
obtaining a reference scanning parameter associated with the ROI, wherein the reference scanning parameter includes a reference scanning direction; and
determining whether the scanning parameter needs to be adjusted by comparing the scanning parameter and the reference scanning parameter, including:
determining a reliability factor of the scanning direction based on a difference between the scanning direction and the reference scanning direction, and a pre-set reference error value of the scanning direction, the pre-set reference error value being an angle value determined according to a portion to be scanned by the imaging device; and
determining whether the scanning parameter needs to be adjusted based on the reliability factor of the scanning direction.

17. The method of claim 16, wherein the determining, based on a contour of the ROI, a scanning parameter associated with the ROI, includes:
determining, in the scout image, a first reference region adjacent to the ROI using a target segmentation model; and
determining, based on the first reference region associated with the ROI, the scanning direction associated with the ROI.

18. The method of claim 17, wherein the reference scanning parameter associated with the ROI includes a reference scanning direction associated with the ROI, and the obtaining a reference scanning parameter associated with the ROI, includes:
determining, in the scout image, a second reference region adjacent to the ROI or the first referent region using the target segmentation model;
determining, based on the first reference region and the second reference region associated with the ROI, the reference scanning direction associated with the ROI.

19. The method of claim 18, wherein the determining the reference scanning direction associated with the ROI includes:
determining a first point on a contour of the second reference region;
determining, based on the first point on the contour of the second reference region, a second point on a contour of the first reference region, the second point being an intersection point of the contour of the first reference region and a feature line passing through the first point; and
determining, based on the second point and a third point on the contour of the first reference region, the reference scanning direction.

20. The method of claim 16, wherein the scanning direction defines a tilting angle of a gantry of the imaging device or a direction along which the radiation beams or the pulses or radio waves are emitted.

* * * * *